(12) United States Patent  
Abreu

(10) Patent No.: US 11,986,420 B2  
(45) Date of Patent: May 21, 2024

(54) ARTICLES TO MANIPULATE THE TEMPERATURE OF BODY EXTREMITIES

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

(*) Notice: Subject to any disclaimer, the term of this patent is extended or adjusted under 35 U.S.C. 154(b) by 0 days.

(21) Appl. No.: 15/062,633

(22) Filed: Mar. 7, 2016

(65) Prior Publication Data

US 2016/0262924 A1 Sep. 15, 2016

Related U.S. Application Data

(60) Provisional application No. 62/131,070, filed on Mar. 10, 2015.

(51) Int. Cl.
*A61F 7/00* (2006.01)
*A41D 19/00* (2006.01)
(Continued)

(52) U.S. Cl.
CPC .......... *A61F 7/007* (2013.01); *A41D 19/0027* (2013.01); *A43B 3/34* (2022.01);
(Continued)

(58) Field of Classification Search
CPC .... A61F 7/007; A61F 7/02; A61F 2007/0093; A61F 2007/008; A61F 2007/0036; A61F 2007/0047; A61F 2007/0037; A61F 2007/0096; A61F 2007/0086; A61F 2007/0046; A61F 2007/0045; A61F 2007/0233; A61F 2007/0075; A43B 7/04; A43B 3/0005
See application file for complete search history.

(56) References Cited

U.S. PATENT DOCUMENTS 2,298,299 A * 10/1942 Joy ........................ A43B 7/025
219/211
4,950,868 A 8/1990 Moss et al.
(Continued)

OTHER PUBLICATIONS

International Preliminary Report on Patentability dated Sep. 21, 2017, issued in International Application No. PCT/US2016/021168; 15pp.
(Continued)

*Primary Examiner* — Kaitlyn E Smith
*Assistant Examiner* — Yasamin Ekrami
(74) *Attorney, Agent, or Firm* — Studebaker & Brackett PC

(57) ABSTRACT

Temperature of the extremities is a significant factor in temperature control of the body due to the presence of thermal receptors in the extremities. The brain uses signals from these thermal receptors as an indication of environmental conditions, and responds accordingly. Thermal monitoring of extremities and adjustment of extremity temperature are valuable in controlling body temperature, leading to a more optimum body temperature in an array of environmental conditions. Devices, such as a wearable article, and an apparatus to monitor the temperature of extremities, adjust the temperature of the extremities in response to the monitored temperature.

21 Claims, 28 Drawing Sheets

(51) Int. Cl.
*A43B 3/34* (2022.01)
*A43B 3/35* (2022.01)
*A43B 7/00* (2006.01)
*A61F 7/02* (2006.01)

(52) U.S. Cl.
CPC ............... *A43B 3/35* (2022.01); *A43B 7/005* (2013.01); *A61F 7/02* (2013.01); *A61F 2007/0036* (2013.01); *A61F 2007/0037* (2013.01); *A61F 2007/0045* (2013.01); *A61F 2007/0046* (2013.01); *A61F 2007/0047* (2013.01); *A61F 2007/0054* (2013.01); *A61F 2007/0075* (2013.01); *A61F 2007/008* (2013.01); *A61F 2007/0086* (2013.01); *A61F 2007/0091* (2013.01); *A61F 2007/0093* (2013.01); *A61F 2007/0096* (2013.01); *A61F 2007/0233* (2013.01)

(56) References Cited

U.S. PATENT DOCUMENTS

| | | | | |
|---|---|---|---|---|
| 5,032,705 | A * | 7/1991 | Batcheller | A41D 13/0051 219/211 |
| 8,658,943 | B1 * | 2/2014 | Larsen | A61F 7/02 219/211 |
| 2002/0026226 | A1 * | 2/2002 | Ein | A61F 7/007 607/108 |
| 2004/0118831 | A1 * | 6/2004 | Martin | A43B 3/0005 219/494 |
| 2005/0127057 | A1 * | 6/2005 | Rock | A41D 31/0038 219/211 |
| 2008/0132816 | A1 * | 6/2008 | Kane | A61H 7/001 601/152 |
| 2008/0197126 | A1 * | 8/2008 | Bourke | A43B 7/025 219/634 |
| 2009/0012436 | A1 * | 1/2009 | Lanfermann | A61N 1/36003 602/2 |
| 2009/0149928 | A1 * | 6/2009 | Relin | A61F 7/02 607/96 |
| 2009/0326622 | A1 | 12/2009 | Johnson et al. | |
| 2010/0057168 | A1 * | 3/2010 | Slade | A61F 7/007 607/99 |
| 2010/0210982 | A1 * | 8/2010 | Balachandran | A61H 9/0078 601/152 |
| 2011/0071603 | A1 | 3/2011 | Moore | |
| 2012/0018418 | A1 | 1/2012 | Shantha et al. | |
| 2012/0053661 | A1 | 3/2012 | Hooper | |
| 2015/0083704 | A1 * | 3/2015 | Guidry | A41D 19/01535 219/211 |
| 2015/0182375 | A1 * | 7/2015 | Binversie | A61F 7/007 601/18 |

OTHER PUBLICATIONS

Notification of Transmittal of the International Search Report and the Written Opinion of the International Searching Authority; PCT/US2016/021168 dated May 17, 2016.

* cited by examiner

ARTICLES TO MANIPULATE THE TEMPERATURE OF BODY EXTREMITIES

CROSS-REFERENCE TO RELATED APPLICATIONS

This application claims the benefit of priority to U.S. Provisional Patent Application No. 62/131,070, filed on Mar. 10, 2015, which is hereby incorporated by reference in its entirety.

TECHNICAL FIELD

This disclosure relates to devices configured to monitor and manipulate or change the temperature of human extremities.

BACKGROUND

Humans are able to control body temperature through environmental control, e.g., heating and air conditioning systems, by wearing temperature-appropriate clothing, by using heating or cooling blankets and pads, and by ingesting cold or hot liquids. Measurement of body temperature is accomplished separately, by way of oral, axillary, forehead, or rectal thermometers.

SUMMARY

This disclosure provides a wearable article comprising a wearable article body, at least one temperature sensor, a plurality of temperature modification devices; and a processor. The at least one temperature sensor is positioned on or in the wearable article body to measure a temperature of a human extremity and is configured to transmit a temperature signal indicative of the temperature of the human extremity. The plurality of temperature modification devices is positioned on or in the wearable article body adjacent to the human extremity. Each temperature modification device of the plurality of temperature modification devices is configured to receive a control signal and to provide temperature modification of the human extremity based on the control signal. The processor is configured to receive the temperature signal, to determine on the basis of the temperature signal whether the human extremity requires heating or cooling, and to automatically transmit the control signal to the temperature modification device.

Advantages and features of the embodiments of this disclosure will become more apparent from the following detailed description of exemplary embodiments when viewed in conjunction with the accompanying drawings.

DETAILED DESCRIPTION

Figure 1:
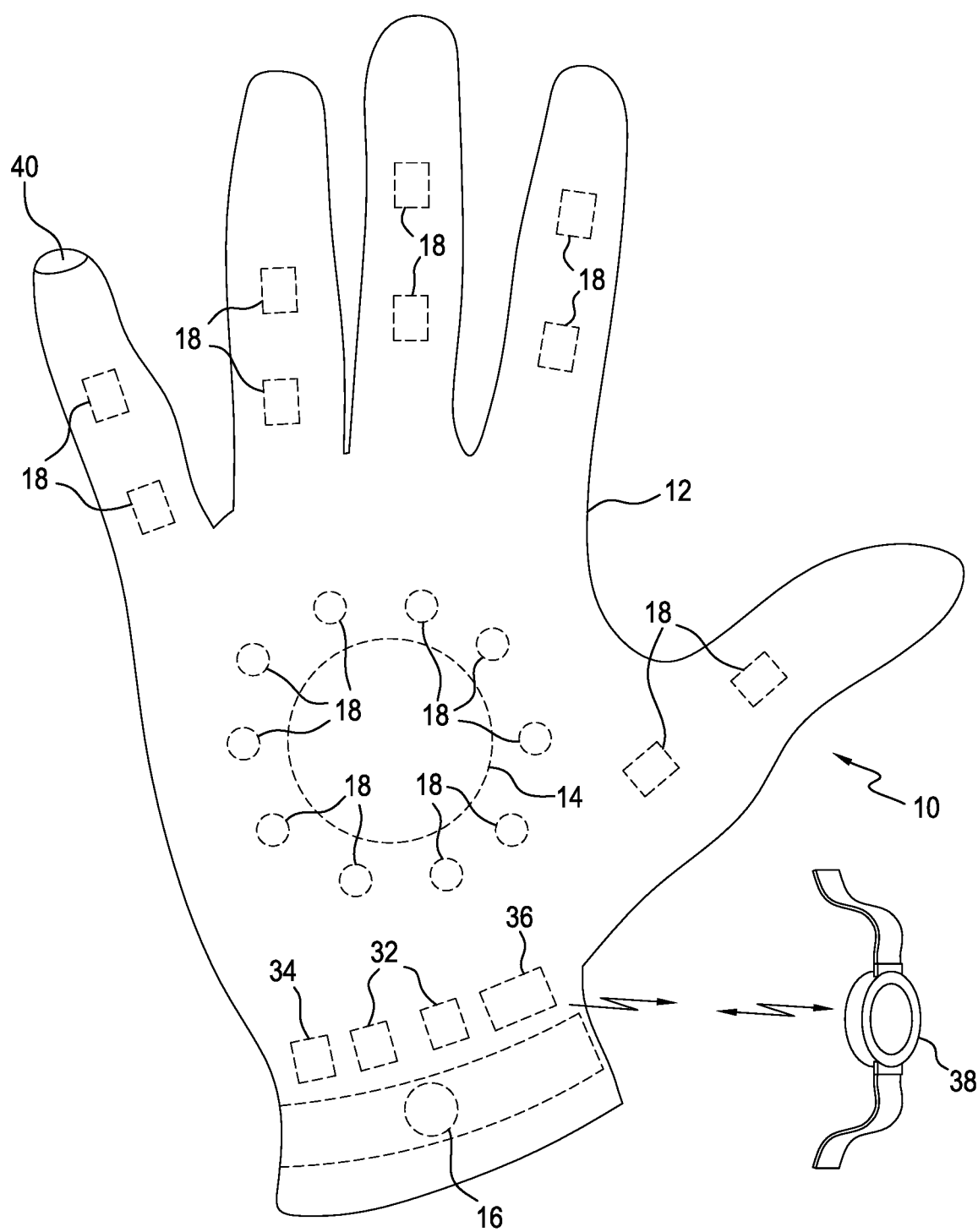
FIG. 1 shows a view of a right hand thermal glove in accordance with an exemplary embodiment of the present disclosure.

Temperature control of the human body is complicated because of how the brain gathers information and reacts to that information. Applicant appreciated through experimentation and analysis that temperature of the extremities is a significant factor in temperature control of the body due to the presence of thermal receptors in the extremities. The brain uses signals from these thermal receptors as an indication of environmental conditions, and responds accordingly. For example, if the hands are cold, the brain considers the entire body to be cold and begins generating heat, such as through shivering. Conversely, if the hands are hot, the brain reacts as though the entire body is hot, and attempts to cool itself, as well as the rest of the body. Applicant recognized through his testing that thermal monitoring of extremities and adjustment of extremity temperature are valuable in controlling body and brain temperature, leading to a more optimum body and brain temperature in an array of environmental conditions. The present disclosure provides devices, such as a wearable article, and apparatus to monitor the temperature of extremities and to adjust the temperature of the extremities in response to the monitored temperature.

Prior art attempts to cool or warm the body, in particular the extremities, have failed to provide useful devices because application of cold or hot devices to a skin surface of the body, in particular the skin surface of the extremities, causes discomfort and even painful sensation. Applicant, who is a medical doctor, recognized and performed experiments that identified a mechanism to inhibit the painful sensation when the skin is exposed to localized cold or hot surfaces.

For thermal stimulus to result in pain some thermal afferent fibers may stimulate the nociceptive system. Applicant recognized and tested that sensory interactions between different nerve fibers carrying different sensations may have inhibitory action, and that special tactile geometry decreases thermal sensations (all ranges of high and low temperature, hot or cold), as a result of specialized stimulation of primary tactile afferent fibers. Applicant further recognized and tested that mechanoreception with application of perpendicular pressure to temperature modification devices (such as resistive, thermoelectric and the like) using micro pumps with low flow and low pressure, resulted in inhibition of pain during thermal stimulus, even to high level thermal stimulus such as 43° C. or low level thermal stimulus such as 15° C.

Studies by Applicant showed that a painful sensation occurred during thermal stimuli (hot at 40° C., or cold at 19° C.,) when temperature modification devices rested against the skin surface in a motionless fashion. However, once vertical movement was applied to the temperature modification devices, vertical meaning approximately perpendicular to the skin surface, the painful sensation was inhibited despite the temperature modification device having the same unchanged temperature level, for a moving device or a motionless device. This test showed that perpendicular motion with minor indentation of the skin surface inhibits the discomfort and suppresses the painful sensation that occur when applying a thermal stimulus directly on the skin surface.

Initially, the thermoelectric devices, heaters, and any temperature modifying device is adapted to reach and maintain a temperature between 33° C. and 34° C., which is considered a baseline temperature. Thermoelectric devices such as Peltier devices and any temperature modifying devices are preferably located in the region of the distal and middle phalanxes. Thermal sensors are preferably located at the base of the fingers and in the palm adjacent to the transition between finger and palm, and thermal sensors preferably measure skin temperature at the base of the fingers or the palm (and are located away from temperature modification devices). It should be understood that a thermoelectric device can contain a thermal sensor to indicate temperature of the thermoelectric device.

Figure 2:
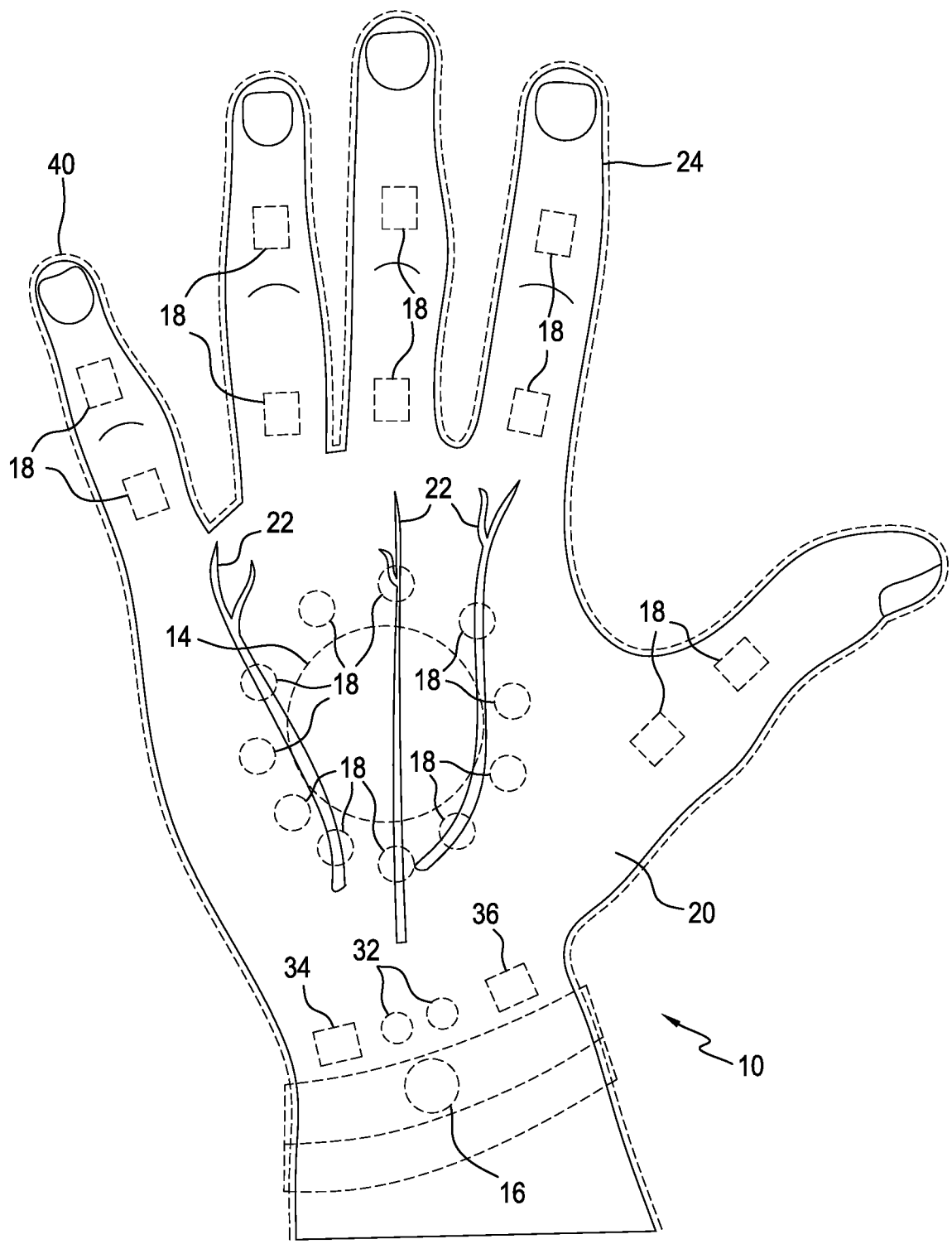
FIG. 2 shows a view of the thermal glove of FIG. 1, with features of the glove shown in dashed lines to show the relationship of glove features to features of an associated hand.

FIGS. 1 and 2 are views of a wearable article in the form of a thermal glove in accordance with an exemplary embodiment of the present disclosure, indicated generally at 10. Glove 10 includes a glove body 12, which can be formed of a natural material such as leather, or an artificial material such as nitrile, latex, nylon, etc., one or more temperature sensors 14 and 16, and a plurality of temperature modification devices 18. Temperature sensors 14 and 16 can be thermopiles or thermocouples, and can be positioned in areas of the extremity sensitive to heat flow and removal, such as on or near to one or more veins, arteries, or blood vessels 22. It should be understood that the term temperature sensor is used as a general term for any device configured to measure thermal energy and to convert the measured thermal energy into a reading indicative of temperature of a human body. Accordingly, other terms for temperature sensor are thermal sensor and heat sensor, Temperature modification devices 18 can be bi-directional thermoelectric devices that are configured to provide heating and cooling, resistive heaters, fluid systems, or other devices configured to change the temperature.

Glove 10 further includes a power supply 32, which can be in the form of batteries, a controller or processor 34, and a transceiver, transmitter, or receiver 36 for communication with a separate electronic device 38, which can be a laptop, watch, cell phone, tablet, or the like.

Temperature modification devices 18 can be positioned in areas of a hand 20 proximate to one or more veins, arteries, or blood vessels 22, in addition to areas of fingers 24, which can include a thumb, to optimize flow of heat throughout hand 20, either to or from temperature modification devices 18. It should be understood that the configuration of temperature modification devices 18 shown in FIGS. 1 and 2, as well as other temperature modifications devices shown throughout this disclosure, is exemplary, and there are an infinite number of locations and configurations for such devices. It should also be understood that such devices can be placed in areas adjacent to a palm of hand 20 as well as a back of a hand 20.

Though glove 10 shows temperature sensors 14 and 16, both of which are positioned in areas of high blood flow, it should be understood that temperature sensors can be located throughout glove 10, including areas adjacent to fingers 24.

In operation, at least one temperature sensor, such as temperature sensor 14 or 16, sends signals representative of a temperature measurement to processor 34. Processor 34 determines, in view of, for example, environmental conditions by way of an ambient temperature sensor 40, which can be positioned on an external surface of glove 10, such as on an exterior surface of a finger of the glove in an area near a tip of a finger or adjacent a finger nail, and the temperature of hand 20, whether temperature modification of hand 20 and/or fingers 24 is needed. If processor 34 determines that temperature conditions of hand 20 are cooler or warmer than a predetermined hand temperature or a predetermined combination of temperatures, e.g., an ambient temperature of 5 degrees Celsius and a hand temperature of 30 degrees Celsius, then processor 34 can automatically trigger generation of heat in glove 10. It should be understood that glove 10 can be configured to control all temperature modification devices 18, individual temperature modification devices 18, or groups of temperature modification devices 18. Such groups can be configured by density, i.e., a subset of temperature modification devices 18 spread over the entirety of hand 20, or by location, such as a base of a thumb or the palm of hand 20. Though glove 10 can be controlled via processor 34, separate electronic device 38 can be configured to receive data via transceiver 36 and then to transmit control signals to transceiver 36 that are then sent to processor 34. These signals are then used to change the operation of temperature modification devices 18. For example, a user may determine that his or her hands are cold, and by using a program or module built into separate electronic device 38, the user can change the temperature of temperature modification devices 18 manually. It should be understood that ambient temperature sensor 40 can be remotely located from glove 10. For example, ambient temperature sensor 40 can be positioned on or in a cell phone or a watch, an external temperature meter, and other devices. In another embodiment, glove 10 can receive information or signals wirelessly from a weather service that includes current ambient temperature of the region nearest the user. In another embodiment, ambient temperature is provided from a remote device by a wired connection.

Figure 3:
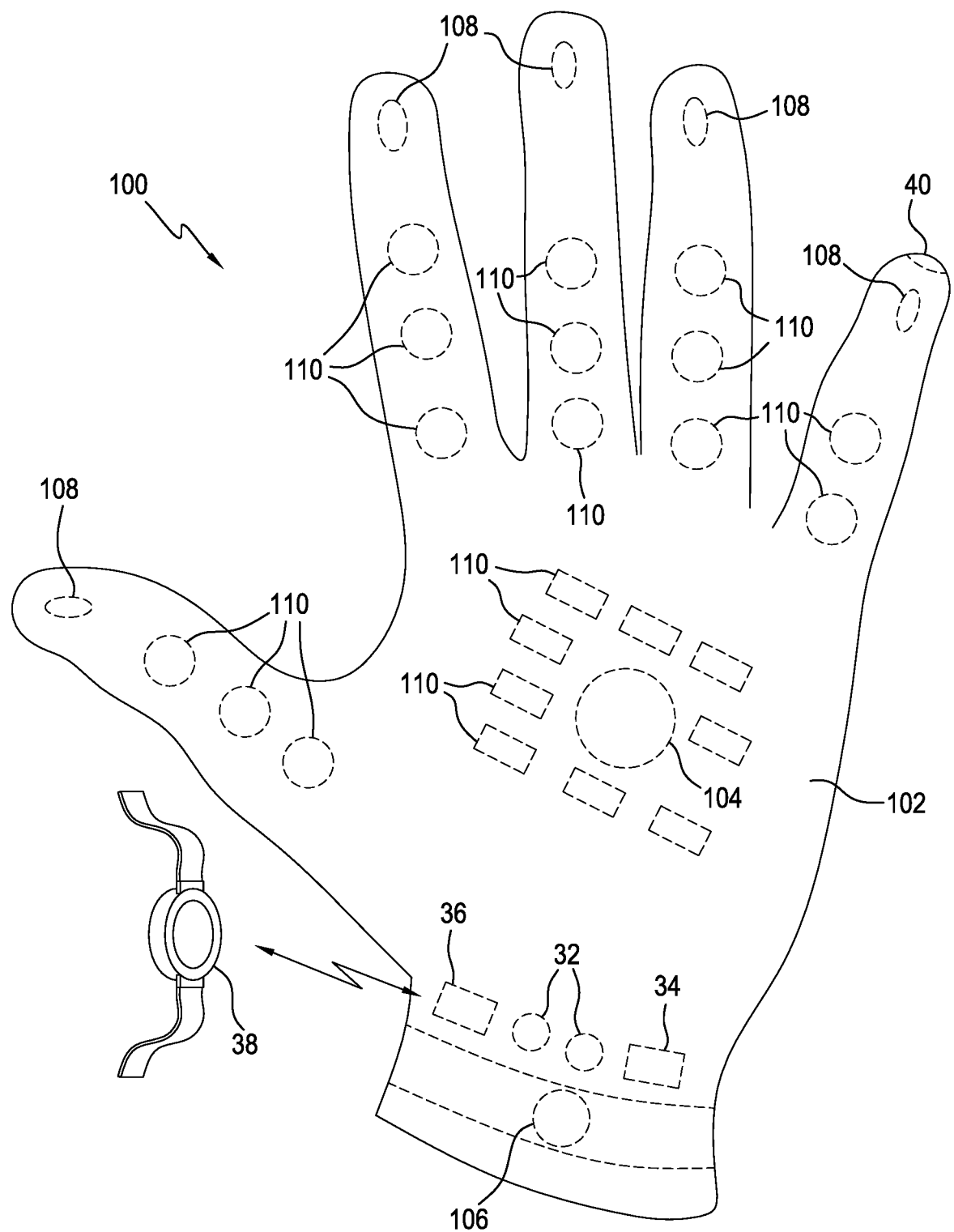
FIG. 3 shows a view of a left hand thermal glove in accordance with an exemplary embodiment of the present disclosure.
Figure 4:
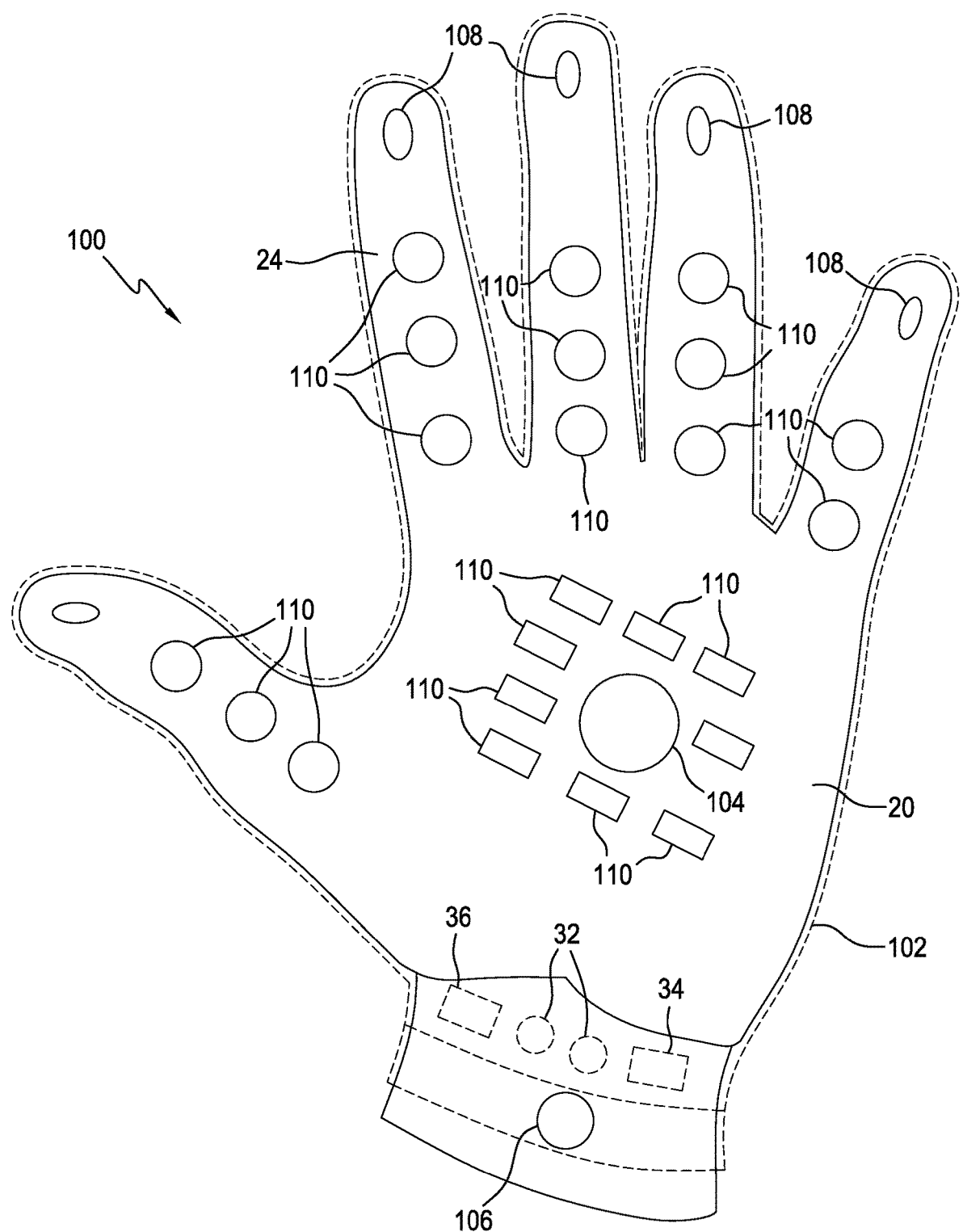
FIG. 4 shows a view of the thermal glove of FIG. 3, with features of the glove shown in dashed lines to show the relationship of glove features to features of an associated hand.
Figure 5:
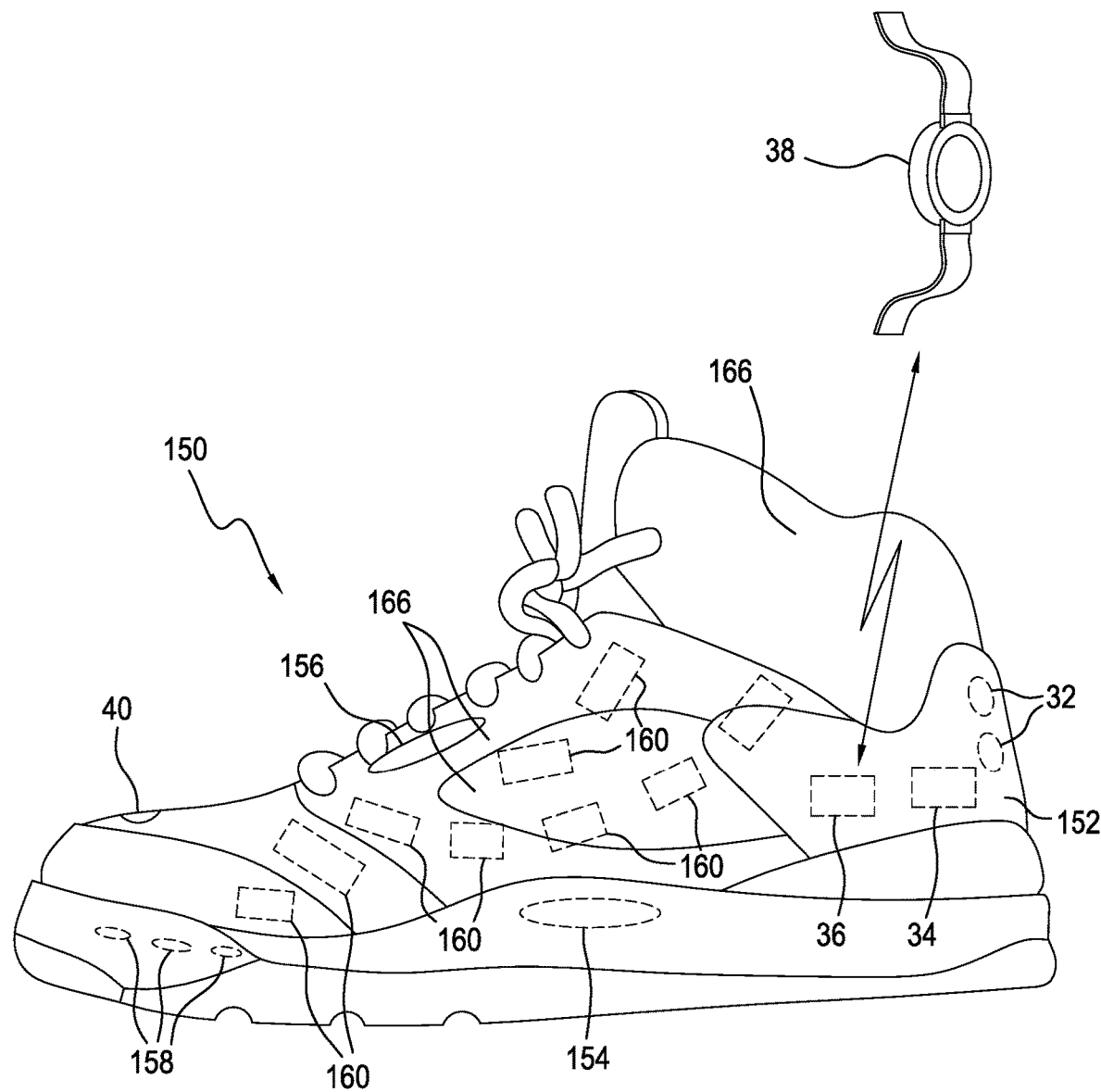
FIG. 5 shows a view of a thermal shoe in accordance with an exemplary embodiment of the present disclosure.
Figure 6:
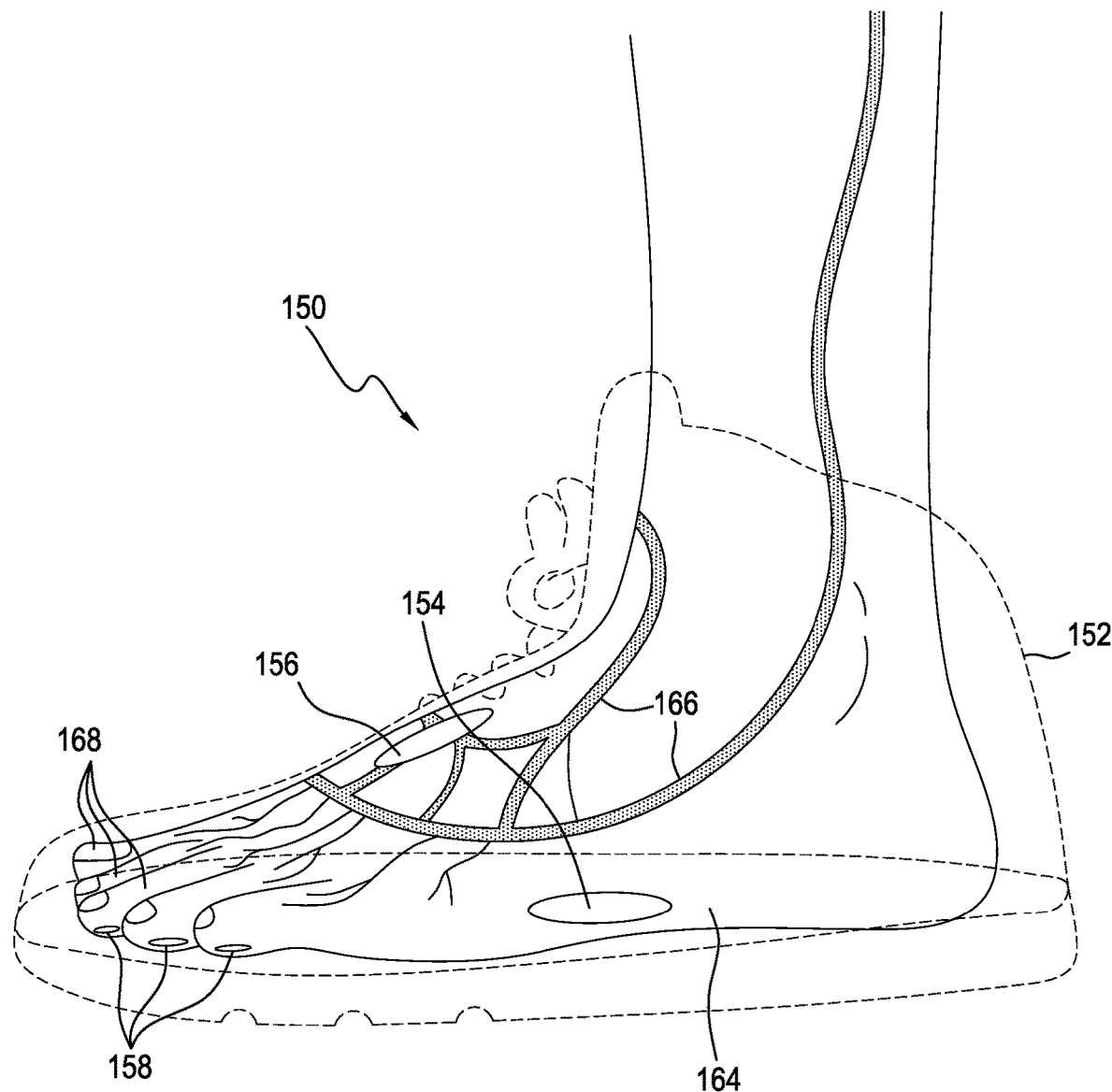
FIG. 6 shows a view of the thermal shoe of FIG. 5, with features of the shoe shown in dashed lines to show the relationship of show features to features of an associated foot.
Figure 7:
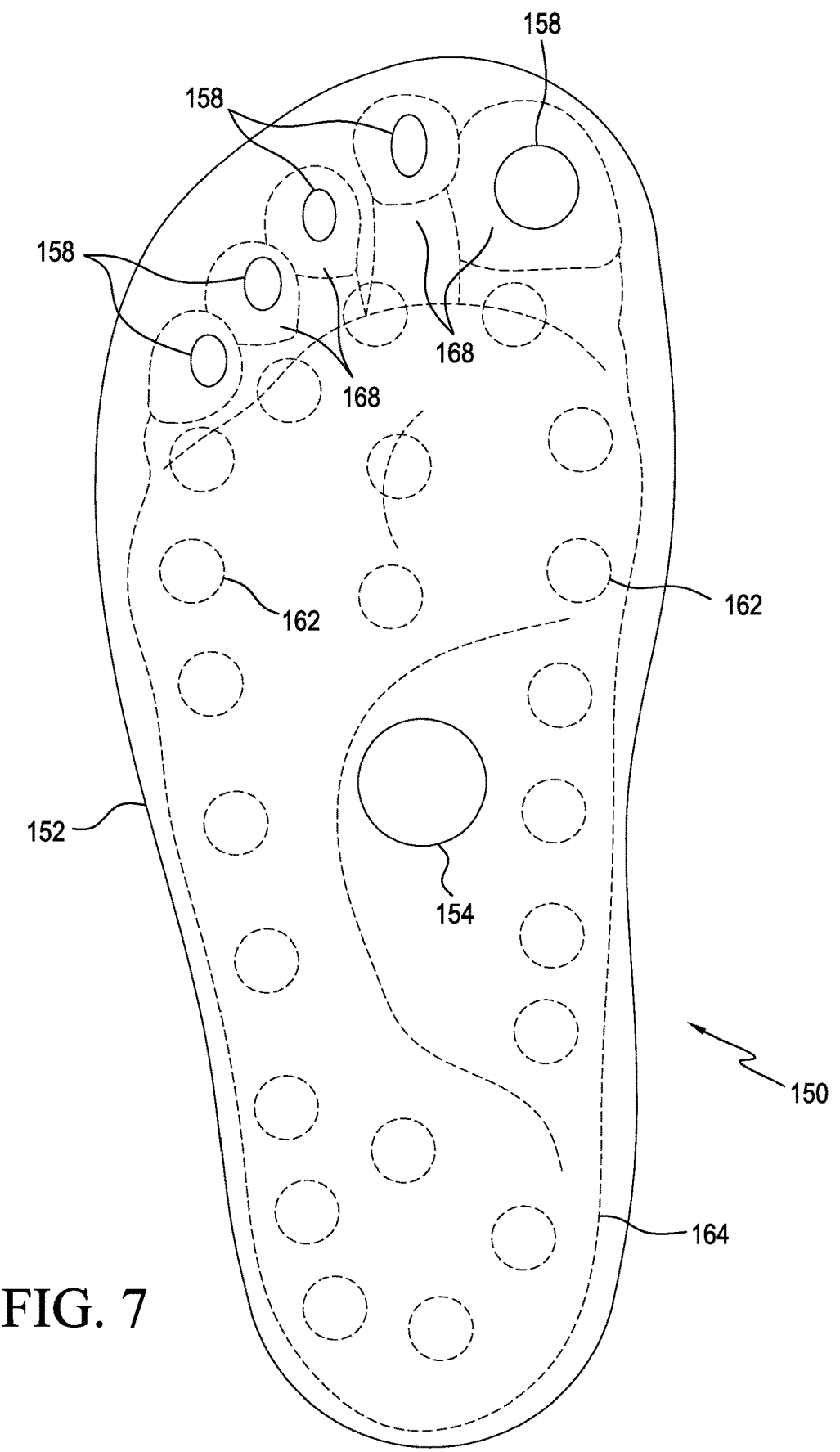
FIG. 7 shows a bottom view of the shoe of FIG. 5, with the associated foot shown in dashed lines.
Figure 8:
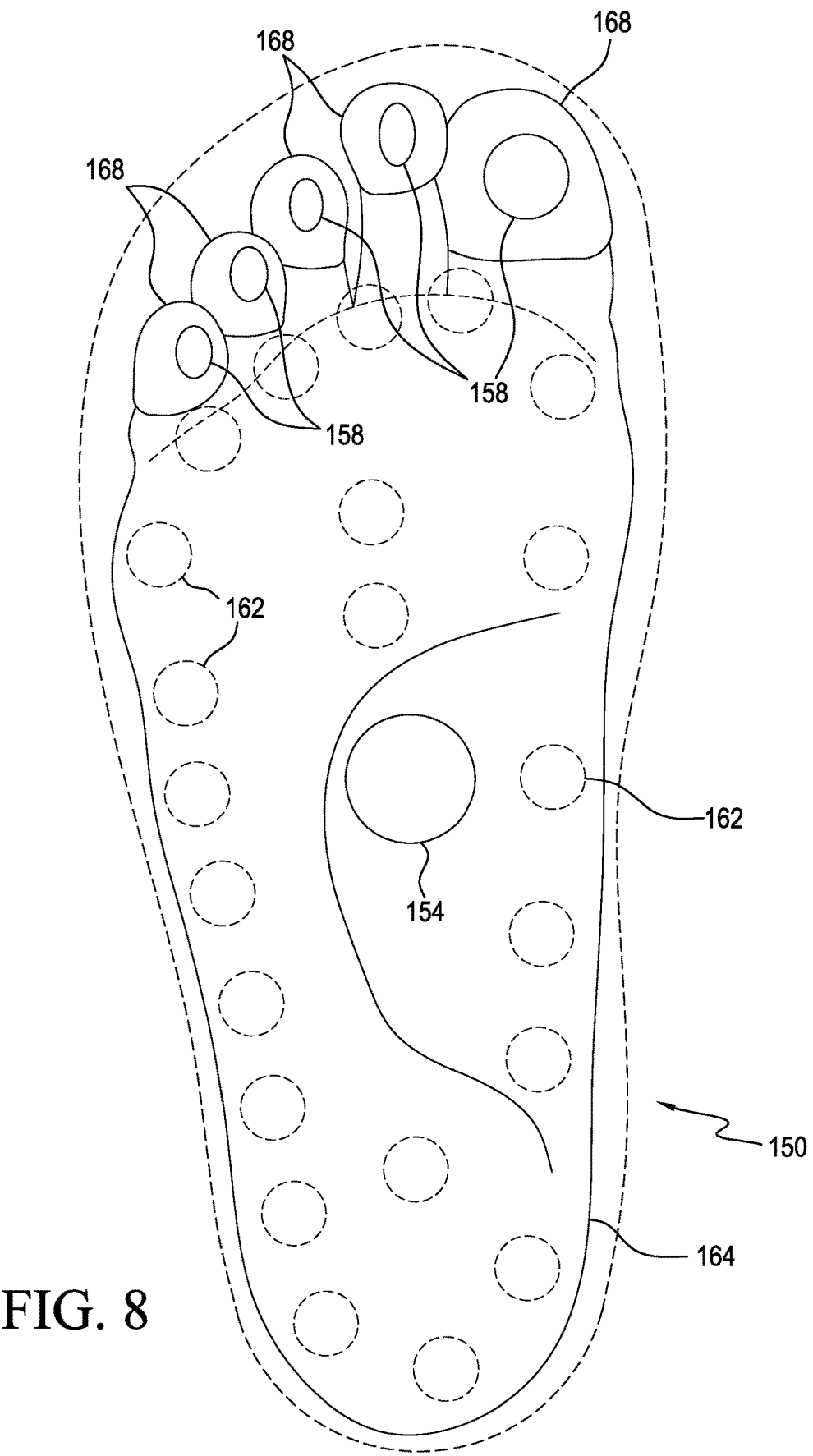
FIG. 8 shows a bottom view of the shoe of FIG. 5, with features of the shoe shown in dashed lines to show the relationship of shoe features to features of the associated foot.
Figure 9:
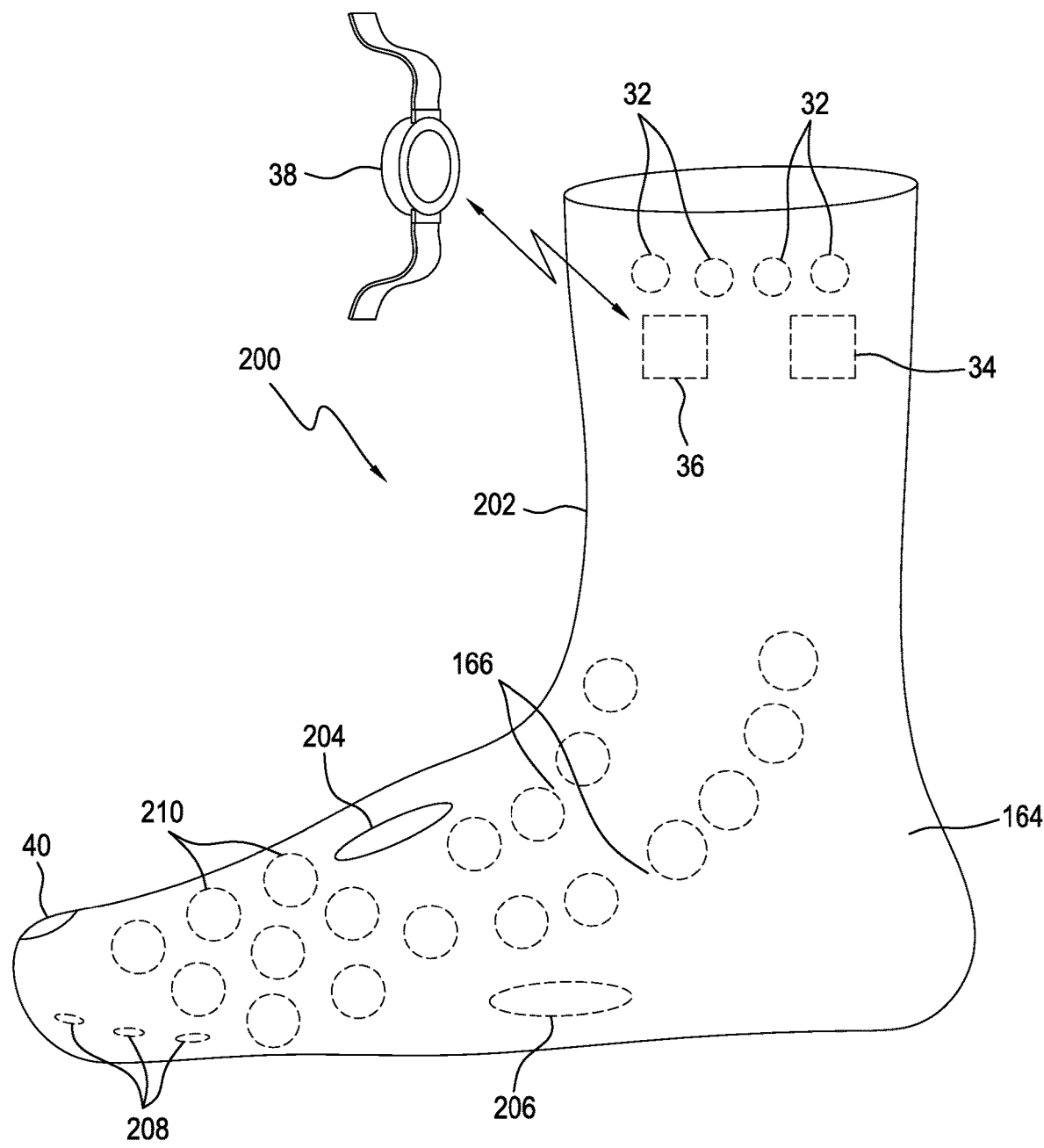
FIG. 9 shows a view of a thermal sock in accordance with an exemplary embodiment of the present disclosure.
Figure 10:
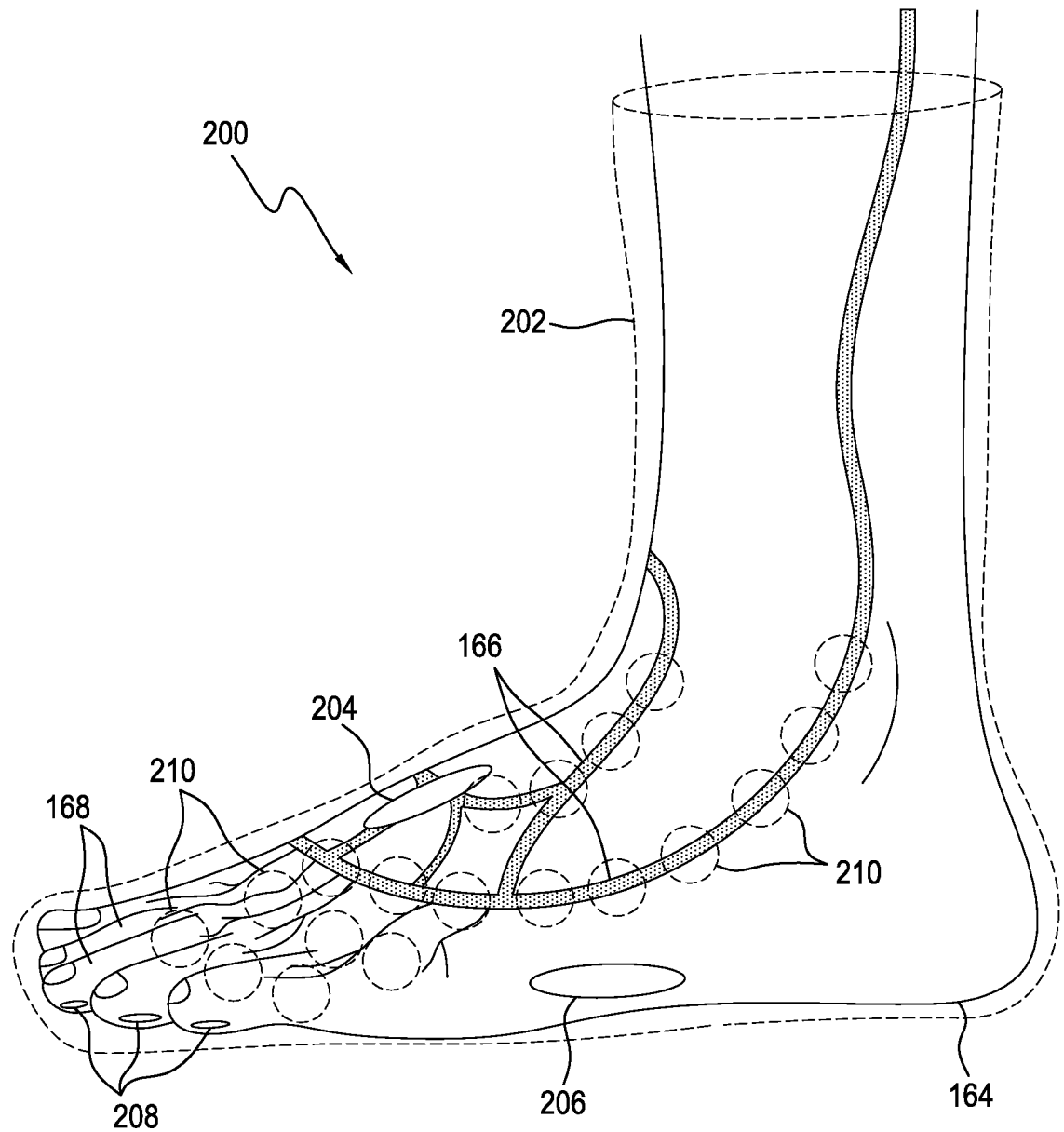
FIG. 10 shows a view of the thermal sock of FIG. 9, with features of the sock shown in dashed lines to show the relationship of sock features to features of an associated foot.
Figure 11:
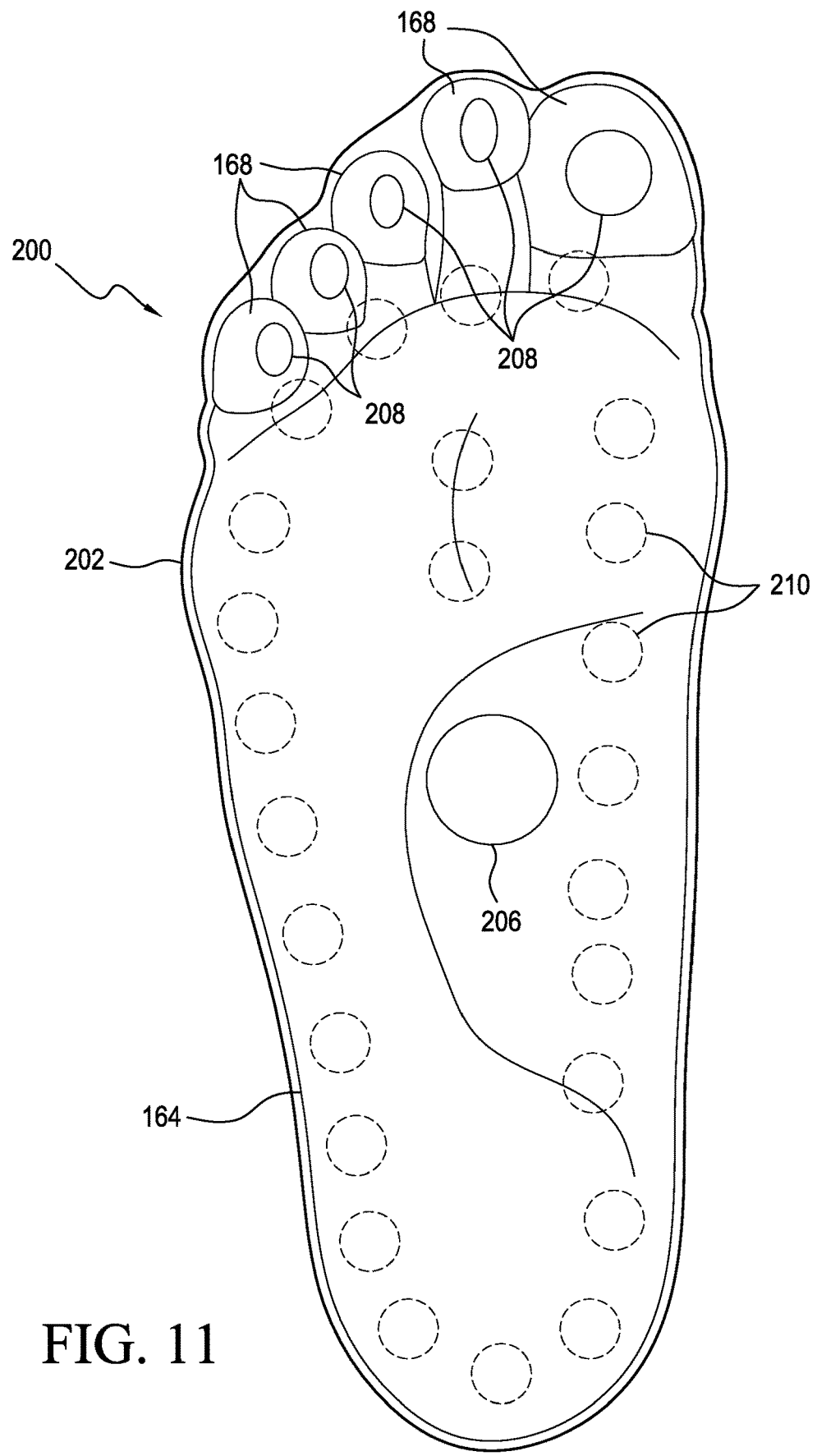
FIG. 11 shows a bottom view of the sock of FIG. 9, with the associated foot shown in muted lines.
Figure 12:
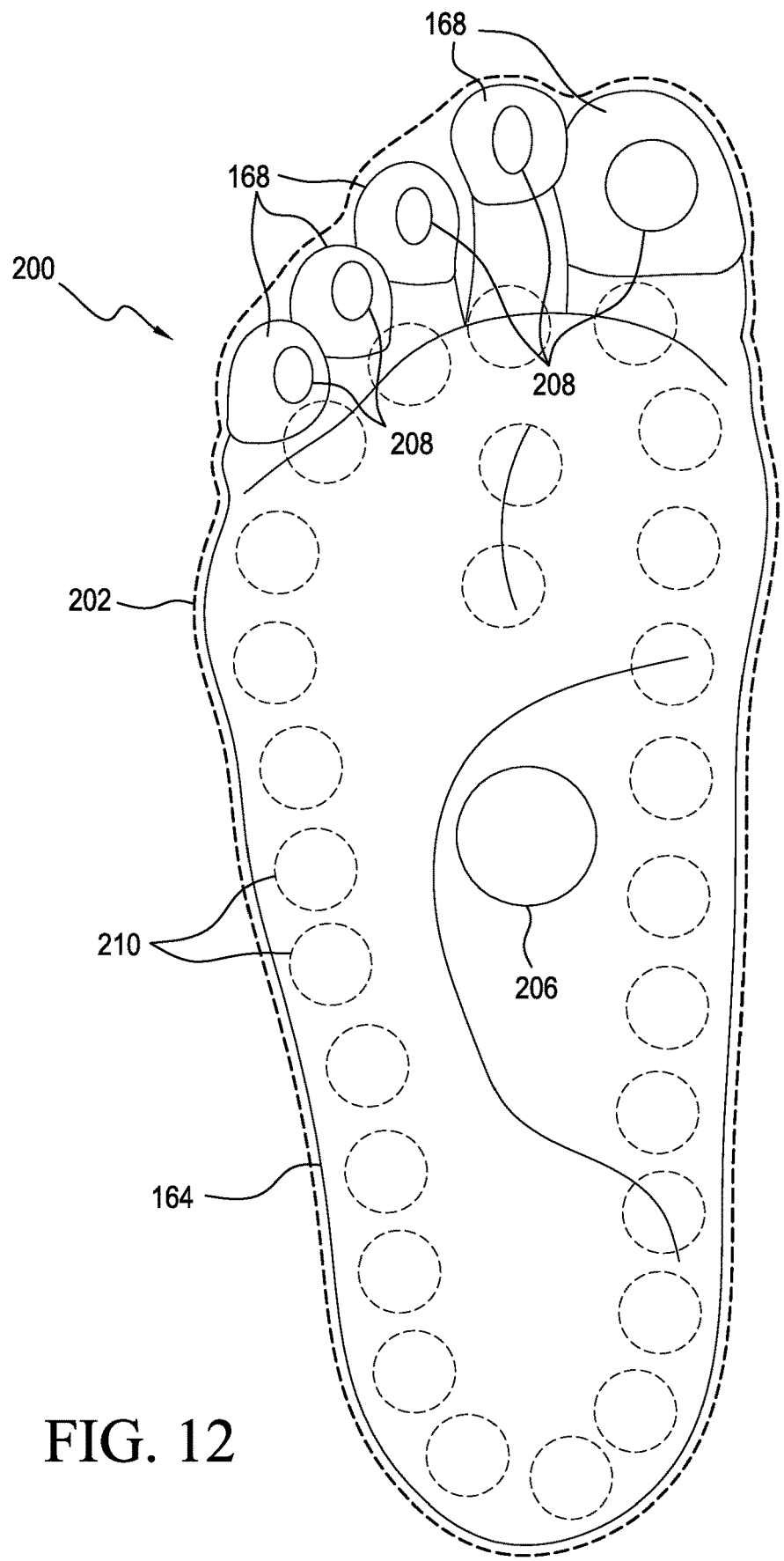
FIG. 12 shows a bottom view of the sock of FIG. 9, with features of the sock shown in dashed lines to show the relationship of sock features to features of the associated foot.

FIGS. 3 and 4 are views of a thermal glove in accordance with an exemplary embodiment of the present disclosure, indicated generally at 100. Glove 100 includes a glove body 102, which can be formed of a natural material such as leather, or an artificial material such as nitrile, latex, nylon, etc., one or more temperature sensors 104, 106, and 108, and a plurality of temperature modification devices 110. Temperature sensors 104, 106, and 108 can be thermopiles or thermocouples. Temperature modification devices 110 can be bi-directional thermoelectric devices that are configured to provide heating and cooling, resistive heaters, fluid systems, or other devices configured to change the temperature.

Glove 100 further includes power supply 32, controller or processor 34, and transceiver, transmitter, or receiver 36 for communication with separate electronic device 38.

Temperature modification devices 110 can be positioned in areas of a hand 20 proximate to one or more veins, arteries, or blood vessels 22, in addition to areas of fingers 24, to optimize flow of heat throughout hand 20, either to or from temperature modification devices 110. It should be understood that the configuration of temperature modification devices 110 shown in FIGS. 3 and 4 is exemplary, and there are an infinite number of locations and configurations for such devices. It should also be understood that such devices can be placed in areas adjacent to the palm of hand 20 as well as the back of hand 20.

Though glove 10 shows temperature sensors 104, 106, and 108, it should be understood that temperature sensors can be located throughout glove 10, including areas adjacent to fingers 24.

In operation, at least one temperature sensor, such as temperature sensor 104, 106, or 108, sends signals to processor 34. Processor 34 determines, in view of, for example, environmental conditions by way of ambient temperature sensor 40, and the temperature of hand 20, whether temperature modification of hand 20 and/or fingers 24 is needed. If processor 34 determines that temperature conditions of hand 20 are cooler or warmer than a predetermined hand temperature or a predetermined combination of hand and environmental or ambient temperatures, then processor 34 can trigger generation of heat in glove 10.

Though glove 100 can be controlled via processor 34, separate electronic device 38 can be configured to receive data via transceiver 36 and then to transmit control signals to transceiver 36 that are then sent to processor 34. These signals are then used to change the operation of temperature modification devices 110. For example, a user may determine that his or her hands are cold, and by using a program or module built into separate electronic device 38, the user is able to change the temperature of temperature modification devices 110 manually.

FIGS. 5-8 are views of a wearable article in the form of a thermal shoe in accordance with an exemplary embodiment of the present disclosure, indicated generally at 150. Shoe 150 includes a shoe body 152, which can be formed of a natural material such as leather, or an artificial material such as nitrile, latex, nylon, etc., one or more temperature sensors 154, 156, and 158, and a plurality of temperature modification devices 160 and 162. Temperature sensors 154, 156, and 158 can be any thermal or temperature sensors, such as thermistors, infrared thermometers, thermopiles or thermocouples, temperature transducers, resistance thermometer, and the like. Temperature modification devices 160 and 162 can be bi-directional thermoelectric devices that are configured to provide heating and cooling, resistive heaters, fluid systems, infrared emitters, lights, or other devices configured to change the temperature.

Shoe 150 further includes power supply 32, controller or processor 34, and transceiver, transmitter, or receiver 36 for communication with separate electronic device 38.

Temperature modification devices 160 and 162 can be positioned in areas of a foot 164 proximate to one or more veins, arteries, or blood vessels 166, in addition to areas of toes 168, to optimize flow of heat throughout foot 164, either to or from temperature modification devices 160 and 162. It should be understood that the configuration of temperature modification devices 160 and 162 shown in FIGS. 5-8 is exemplary, and there are an infinite number of locations and configurations for such devices. It should also be understood that such devices can be placed in areas adjacent to a sole of foot 164 as well as a top of foot 164. It should be understood that shoe 150 can be configured to control all temperature modification devices 160 and 162, individual temperature modification devices 160 and 162, or groups of temperature modification devices 160 and 162. Such groups can be configured by density, i.e., a subset of temperature modification devices 160 and 162 spread over the entirety of foot 164, or by location, such as a ball of foot 164 or toes 168 of foot 164.

Though shoe 150 shows temperature sensors 154, 156, and 158, it should be understood that temperature sensors can be located throughout shoe 150, including areas adjacent to toes 168.

In operation, at least one temperature sensor, such as temperature sensor 154, 156, or 158, sends signals to processor 34. Processor 34 determines, in view of, for example, environmental conditions by way of ambient temperature sensor 40, which can be positioned on or adjacent a toe 168, including a toenail of toe 168, and the temperature of foot 164, whether temperature modification of foot 164 and/or toes 168 is needed. If processor 34 determines that temperature conditions of foot 164 are cooler or warmer than a predetermined foot temperature or a predetermined combination of temperatures, then processor 34 can trigger generation of heat in shoe 150.

Though shoe 150 can be controlled via processor 34, separate electronic device 38 can be configured to receive data via transceiver 36 and then to transmit control signals to transceiver 36 that are then sent to processor 34. These signals are then used to change the operation of temperature modification devices 160 and 162. For example, a user may determine that his or her feet are cold, and by using a program or module built into separate electronic device 38, the user is able to change the temperature of temperature modification devices 160 and 162 manually.

FIGS. 9-12 are views of a wearable article in the form of a thermal sock in accordance with an exemplary embodiment of the present disclosure, indicated generally at 200. Sock 200 includes a sock body 202, which can be formed of a natural material such as cotton, or an artificial material such as nitrile, latex, nylon, etc., one or more temperature sensors 204, 206, and 208, and a plurality of temperature modification devices 210. Temperature sensors 204, 206, and 208 can be thermopiles or thermocouples. Temperature modification devices 210 can be bi-directional thermoelectric devices that are configured to provide heating and cooling, resistive heaters, fluid systems, or other devices configured to change the temperature.

Sock 200 further includes power supply 32, controller or processor 34, and transceiver, transmitter, or receiver 36 for communication with separate electronic device 38.

Temperature modification devices 210 can be positioned in areas of foot 164 proximate to one or more veins, arteries, or blood vessels 166, in addition to areas of toes 168, to optimize flow of heat throughout foot 164, either to or from temperature modification devices 210. It should be understood that the configuration of temperature modification devices 210 shown in FIGS. 9-12 is exemplary, and there are an infinite number of locations and configurations for such devices. It should also be understood that such devices can be placed in areas adjacent to the sole of foot 164 as well as the top of foot 164. It should be understood that sock 200 can be configured to control all temperature modification devices 210, individual temperature modification devices 210, or groups of temperature modification devices 210. Such groups can be configured by density, i.e., a subset of temperature modification devices 210 spread over the entirety of foot 164, or by location, such as the ball of foot 164 or toes 168 of foot 164.

It should be understood that temperature sensors can be located throughout sock 200, including areas adjacent to toes 168.

In operation, at least one temperature sensor, such as temperature sensor 204, 206, or 208, sends signals to processor 34. Processor 34 determines, in view of, for example, environmental conditions by way of ambient temperature sensor 40, and the temperature of foot 164, whether temperature modification of foot 164 and/or toes 168 is needed. If processor 34 determines that temperature conditions of foot 164 are cooler or warmer than a predetermined foot temperature or a predetermined combination of temperatures, then processor 34 can trigger generation of heat in sock 200.

Though sock 200 can be controlled via processor 34, separate electronic device 38 can be configured to receive data via transceiver 36 and then to transmit control signals to transceiver 36 that are then sent to processor 34. These signals are then used to change the operation of temperature modification devices 210. For example, a user may determine that his or her feet are cold, and by using a program or module built into separate electronic device 38, the user is able to change the temperature of temperature modification devices 210 manually.

Figure 13:
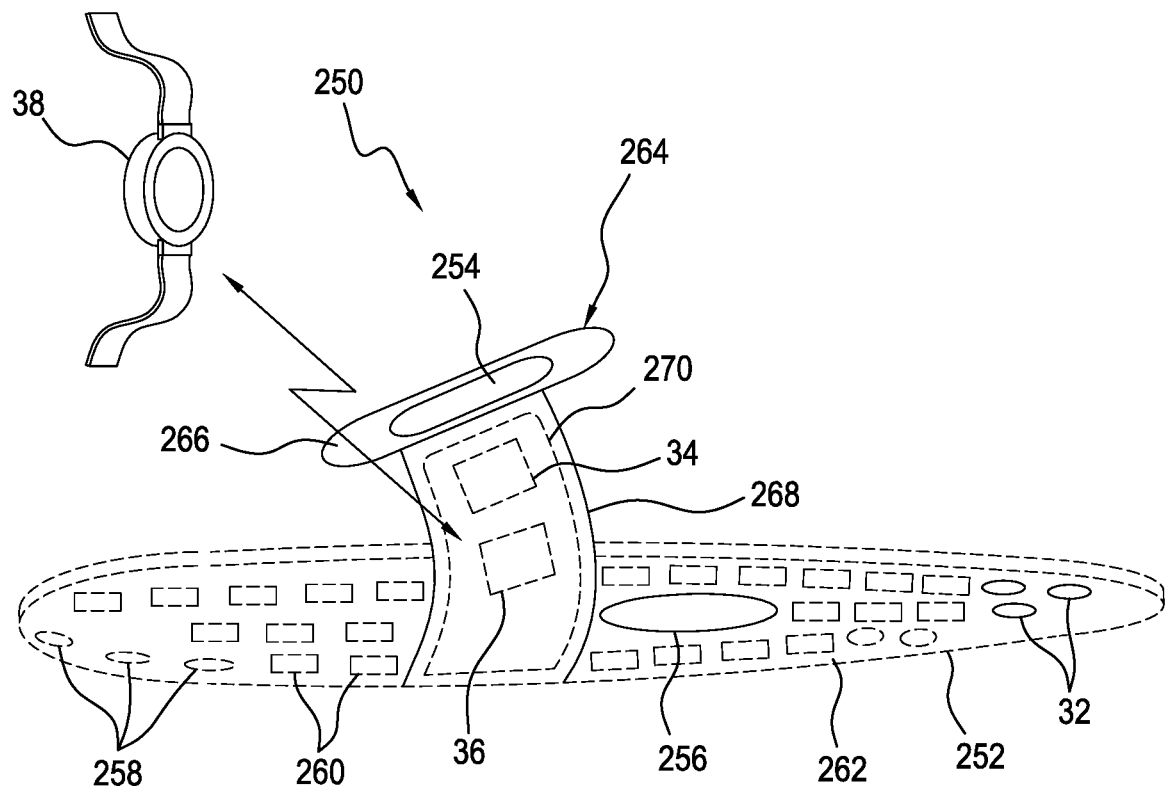
FIG. 13 shows a view of an insert in accordance with an exemplary embodiment of the present disclosure.
Figure 14:
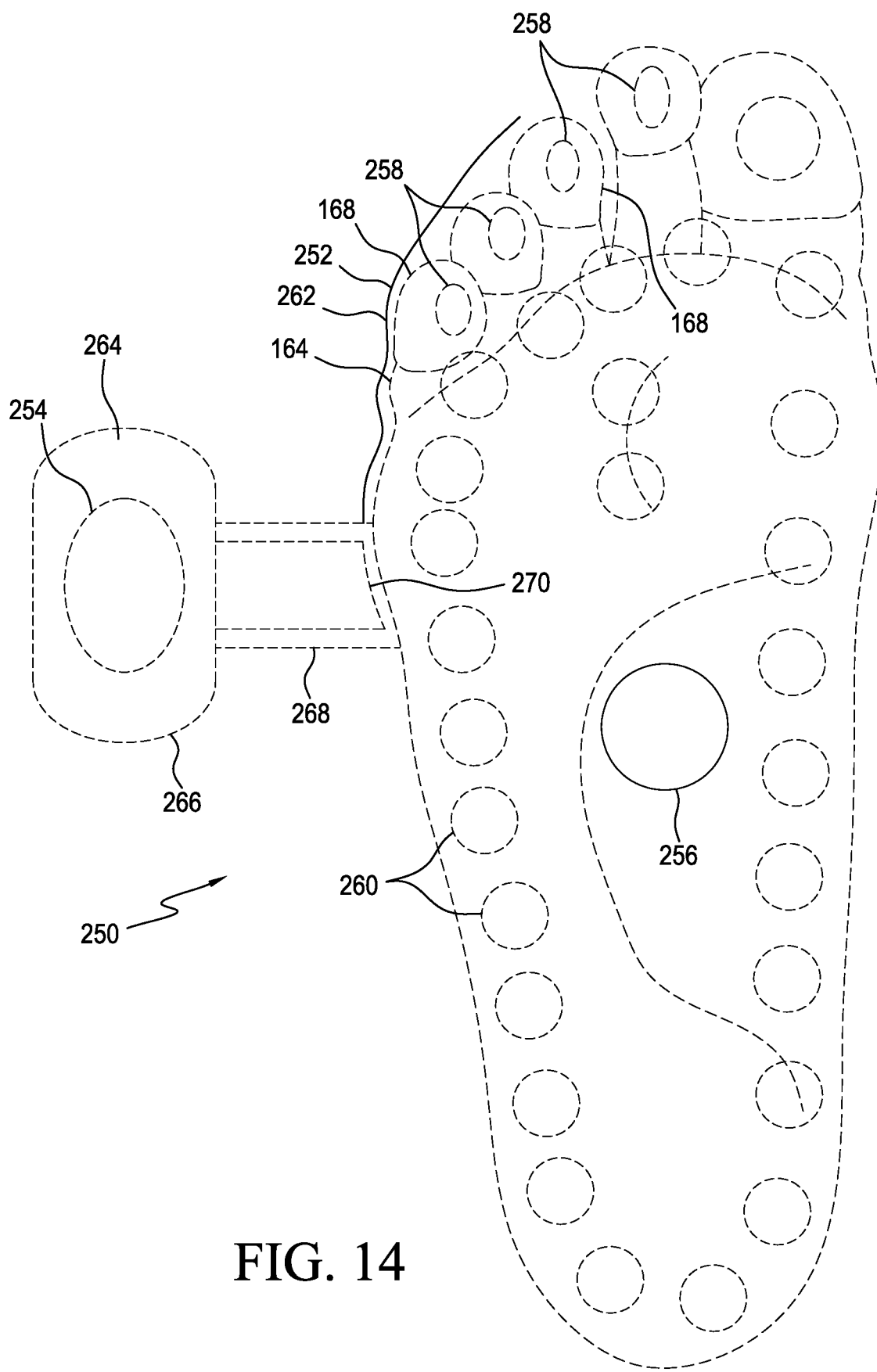
FIG. 14 shows a bottom view of the insert of FIG. 13, with an associated foot shown in dashed lines.
Figure 15:
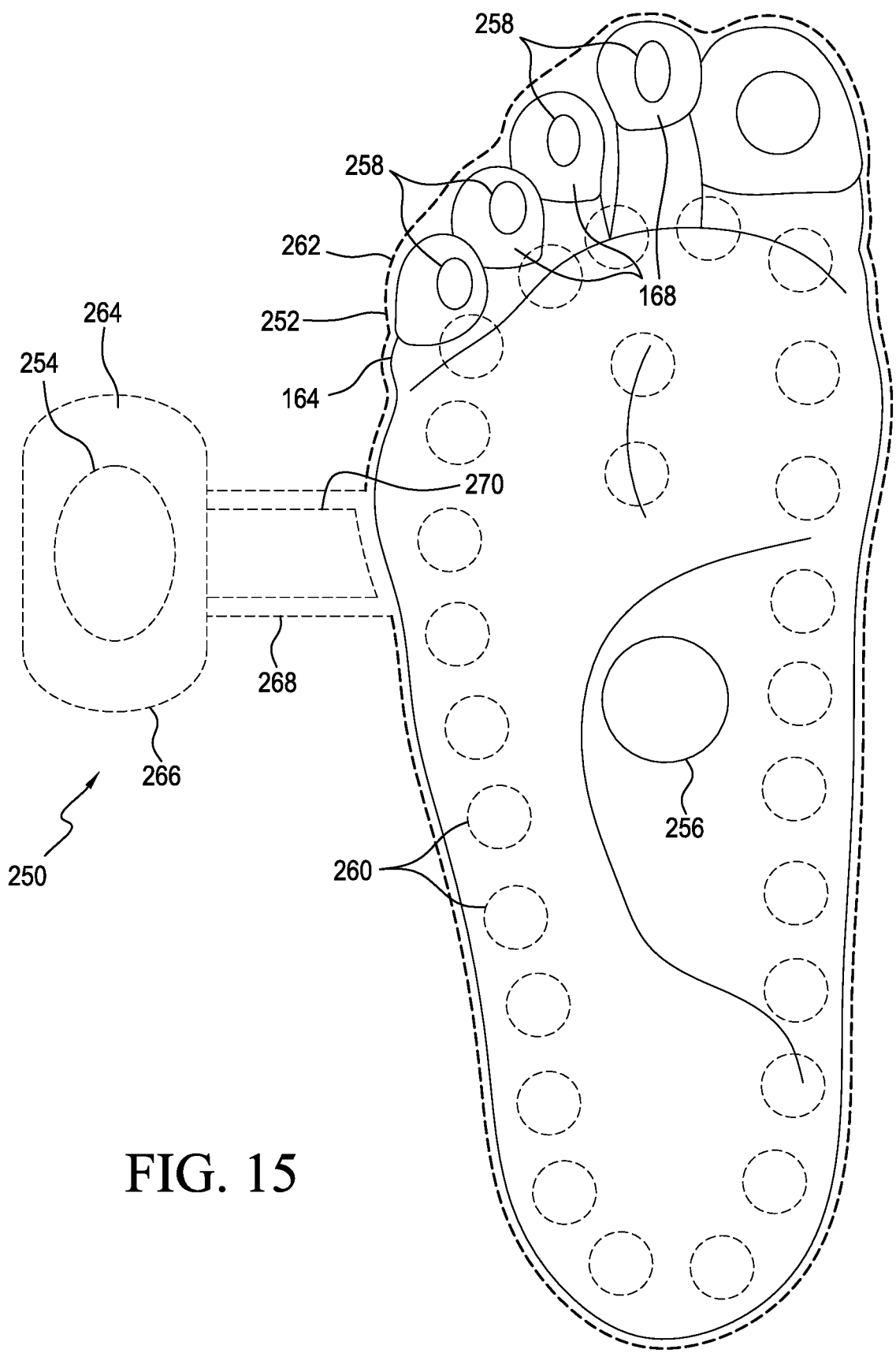
FIG. 15 shows a bottom view of the insert of FIG. 13, with features of the insert shown in dashed lines to show the relationship of insert features to features of the associated foot.

FIGS. 13-15 are views of a wearable article in the form of a shoe or sock insert in accordance with an exemplary embodiment of the present disclosure, indicated generally at 250. Insert 250 includes an insert body 252, which can be formed of a natural material such as cotton, or an artificial material such as nitrile, latex, nylon, etc., one or more temperature sensors 254, 256, and 258, and a plurality of temperature modification devices 260. Temperature sensors 254, 256, and 258 can be thermopiles or thermocouples. Temperature modification devices 260 can be bi-directional thermoelectric devices that are configured to provide heating and cooling, resistive heaters, fluid systems, or other devices configured to change the temperature.

Insert 250 further includes power supply 32, controller or processor 34, and transceiver, transmitter, or receiver 36 for communication with separate electronic device 38.

Temperature modification devices 260 can be positioned in areas of foot 164 proximate to one or more veins, arteries, or blood vessels 166, in addition to areas of toes 168, to optimize flow of heat throughout foot 164, either to or from temperature modification devices 260. It should be understood that the configuration of temperature modification devices 260 shown in FIGS. 13-15 is exemplary, and there are an infinite number of locations and configurations for such devices. It should be understood that insert 250 can be configured to control all temperature modification devices 260, individual temperature modification devices 260, or groups of temperature modification devices 260. Such groups can be configured by density, i.e., a subset of temperature modification devices 260 spread over the entirety of the sole of foot 164, or by location, such as the ball of foot 164 or toes 168 of foot 164.

It should be understood that temperature sensors can be located throughout insert 250, including areas adjacent to toes 168.

Insert 250 further includes a sole portion 262 and a tongue portion 264 that extends from sole portion 262. Tongue portion 264 includes a sensor support 266 and a connector 268. Connector 268 can be configured to include a flexible or bendable material 270 such that tongue portion 264 can be positioned on the top of foot 164 with sole portion 262 on the bottom of foot 164.

In operation, at least one temperature sensor, such as temperature sensor 254, 256, or 258, sends signals to processor 34. Processor 34 determines, in view of, for example, environmental conditions by way of ambient temperature sensor 40, and the temperature of foot 164, whether temperature modification of foot 164 and/or toes 168 is needed. If processor 34 determines that temperature conditions of foot 164 are cooler or warmer than a predetermined foot temperature or a predetermined combination of temperatures, then processor 34 can trigger generation of heat in insert 250.

Though insert 250 can be controlled via processor 34, separate electronic device 38 can be configured to receive data via transceiver 36 and then to transmit control signals to transceiver 36 that are then sent to processor 34. These signals are then used to change the operation of temperature modification devices 260. For example, a user may determine that his or her feet are cold, and by using a program or module built into separate electronic device 38, the user is able to change the temperature of temperature modification devices 260 manually.

Figure 16:
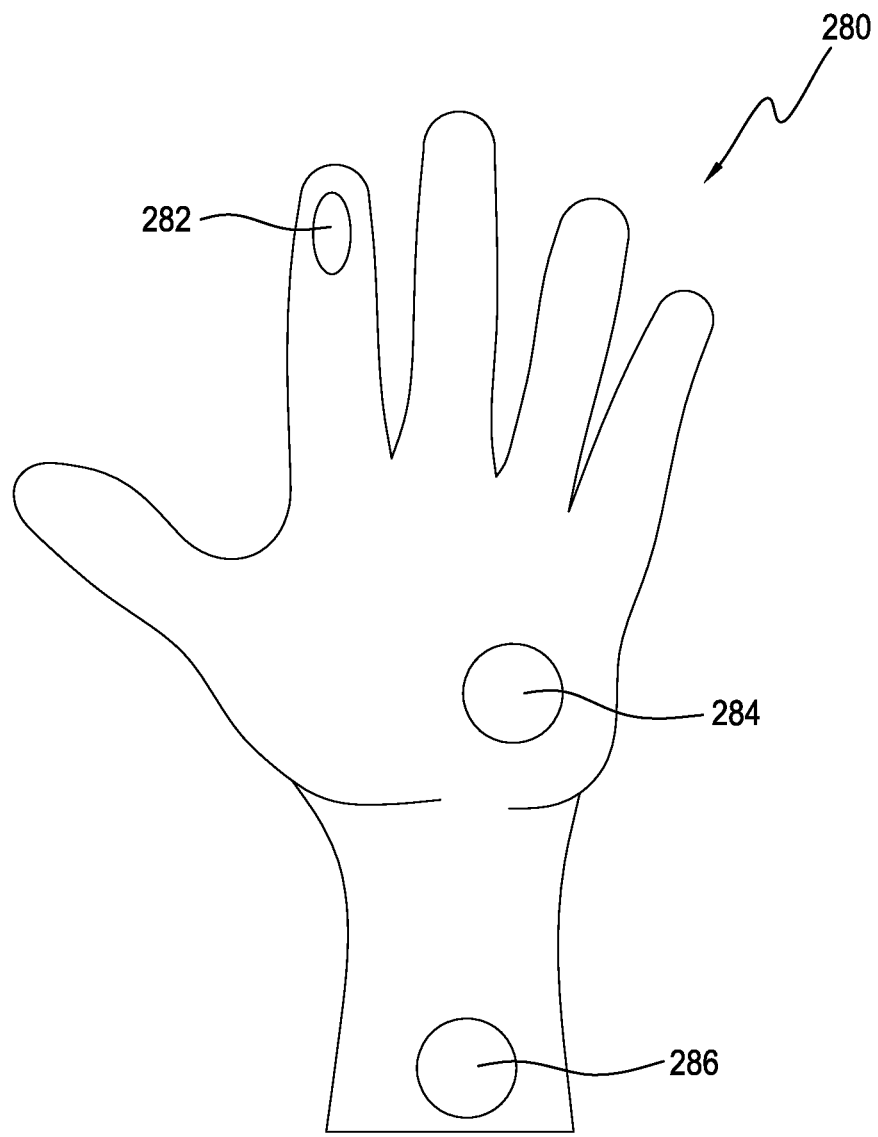
FIG. 16 shows a view of a glove in accordance with an exemplary embodiment of the present disclosure.

FIG. 16 shows a view of a glove, indicated generally at 280, in accordance with an exemplary embodiment of the present disclosure. Glove 280 illustrates general locations for preferred locations of temperature sensors. Glove 280 includes a first temperature sensor 282, a second temperature sensor 284, and a third temperature sensor 286. First temperature sensor 282 is positioned on glove 280 in a location that would be adjacent to a fingertip, e.g., a distal phalanx, if a hand were present in glove 280. Second temperature sensor 284 is positioned on glove 280 in a location that would be adjacent to a palm, e.g., a carpal. Third temperature sensor 286 is positioned on glove 280 in a location that would be adjacent to a distal portion of the forearm, e.g., along the radius and ulna a spaced distance from the location where the radius and ulna connected to the carpals.

Figure 17:
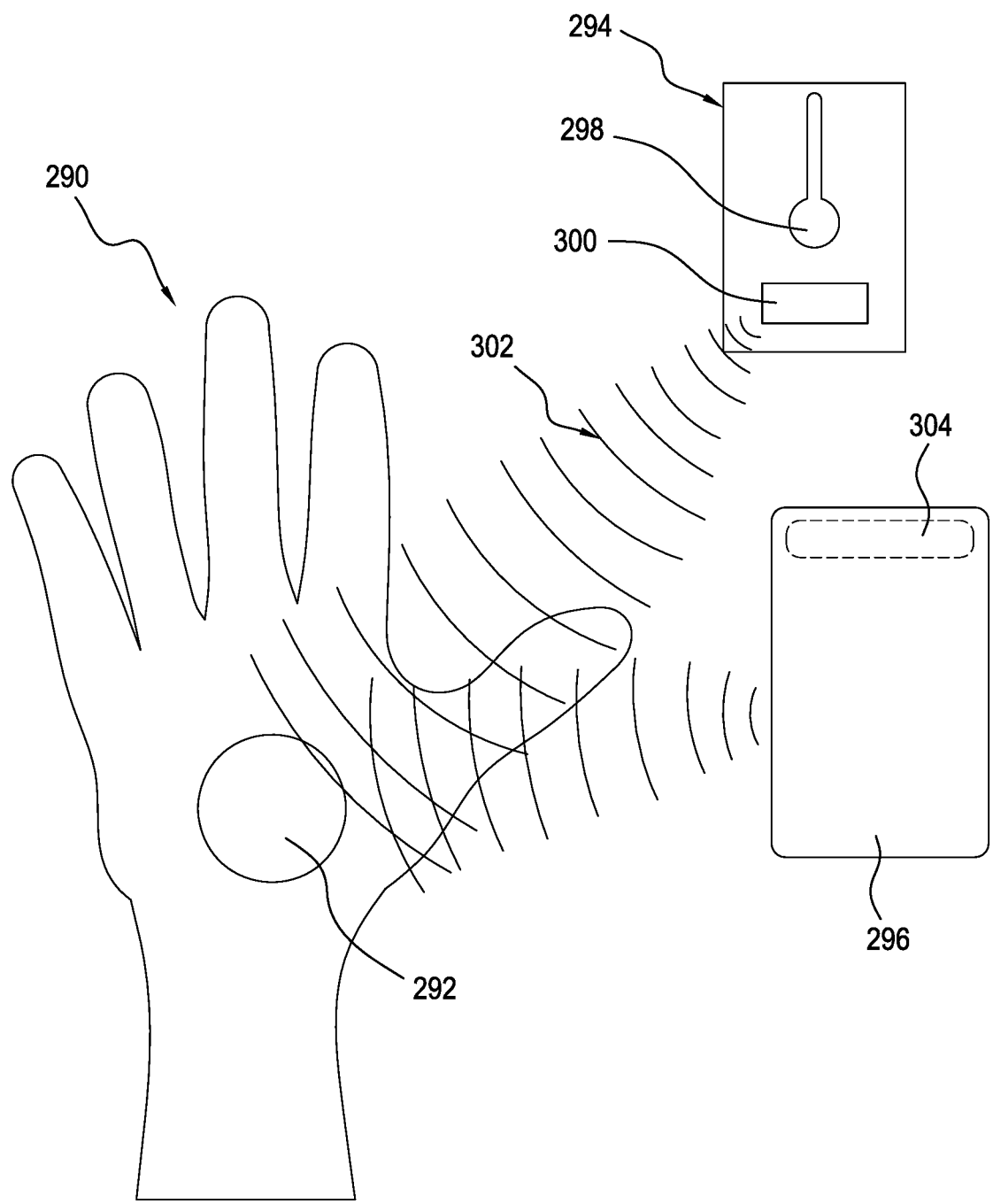
FIG. 17 shows a view of a glove in accordance with another exemplary embodiment of the present disclosure.

FIG. 17 shows a view of a glove, indicated generally at 290, in accordance with another exemplary embodiment of the present disclosure. Glove 290 includes a receiver 292 configured to receive wireless transmissions, which can be near field such as Wi-Fi, intermediate field, such as cellular signals, and far field. FIG. 17 further includes a temperature sensor base station 294 and a mobile communication device 296, such as a cell phone. Temperature sensor base station 294 includes a thermal or temperature sensor 298 configured to measure ambient temperature and a transmitter and antenna 300 configured to transmit a signal 302 representing the measured ambient temperature to receiver 292. Mobile communication device 296 includes a transmitter and antenna 304. Mobile communication device 296 can include an internal ambient temperature sensor or mobile communication device 296 can receive an ambient temperature wireless from a third party, such as a government weather service, and can transmit the information to receiver 292.

Figure 18:
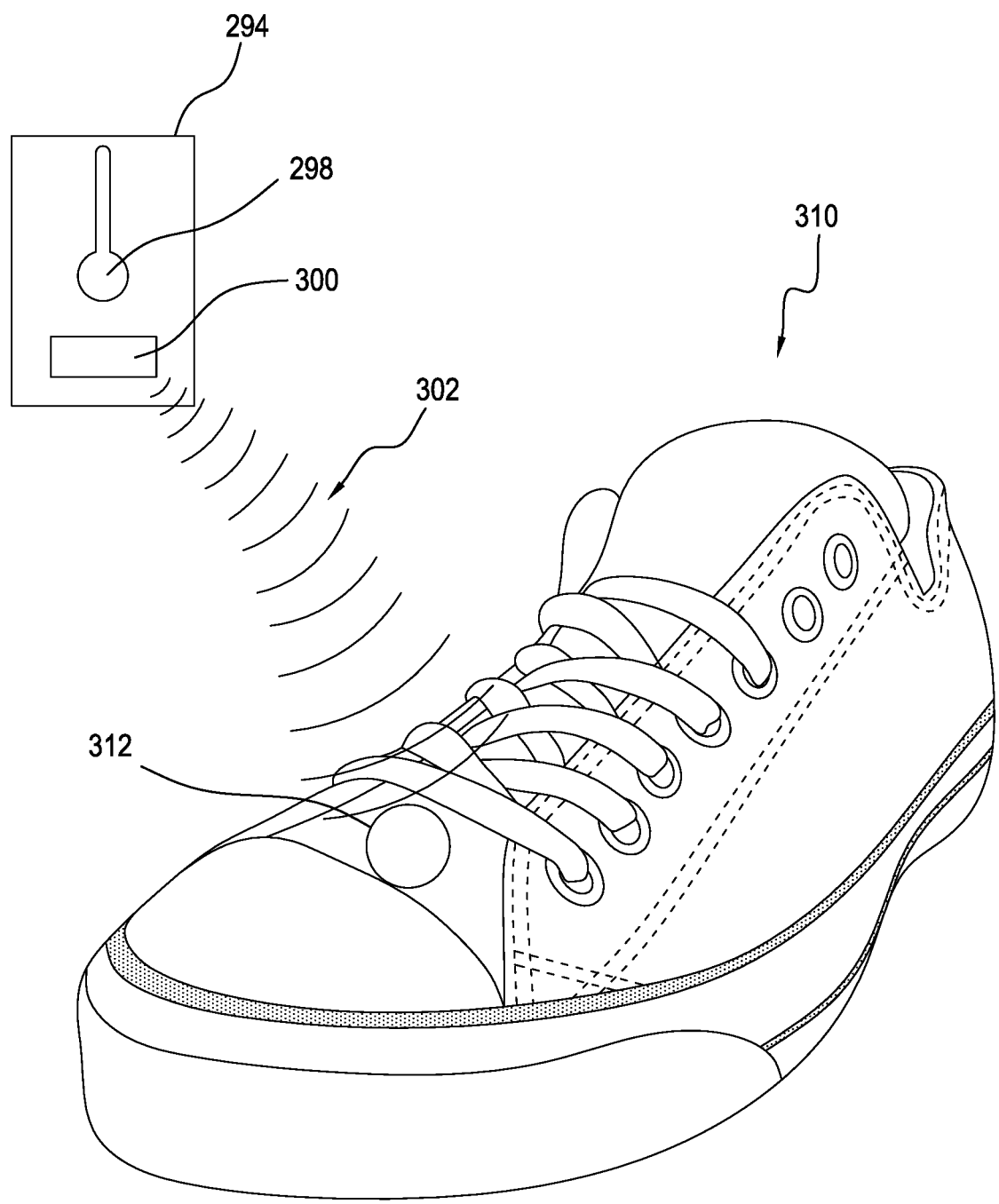
FIG. 18 shows a view of a shoe in accordance with an exemplary embodiment of the present disclosure.

FIG. 18 shows a view of a shoe, indicated generally at 310, in accordance with an exemplary embodiment of the present disclosure. Shoe 310 includes a receiver 312 configured to receive wireless transmissions, which can be near field such as Wi-Fi, intermediate field, such as cellular signals, and far field. FIG. 18 further includes temperature sensor base station 294. Antenna 300 transmits signal 302 representing measured ambient temperature to receiver 292.

Figure 19:
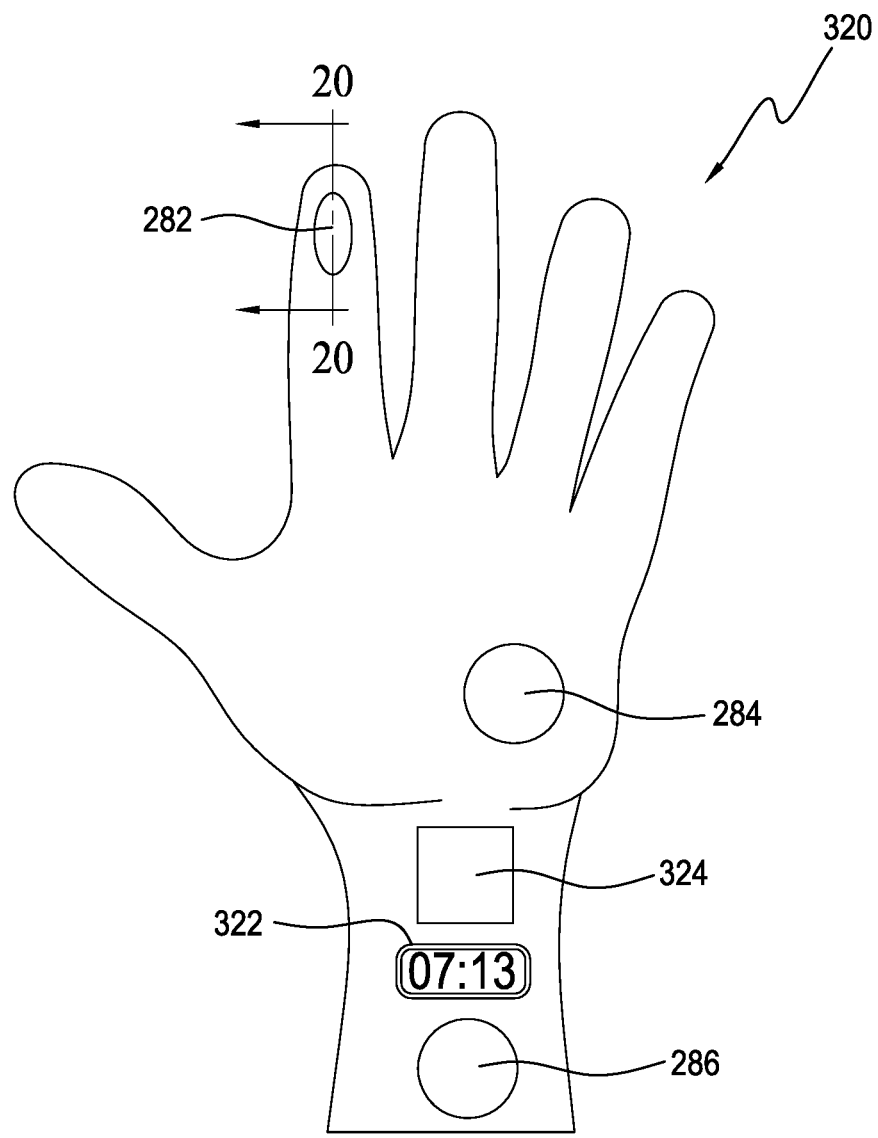
FIG. 19 shows a view of a glove in accordance with a further exemplary embodiment of the present disclosure.

FIG. 19 shows a view of a glove, indicated generally at 320, in accordance with a further exemplary embodiment of the present disclosure. Glove 320 can include one or more previously described temperature sensors 282, 284, and 286, in addition to other temperature sensors, a clock or timer 322, and an input apparatus or device 324. Clock or timer 322 can be used to adjust periods of stimulation and quiet periods of the temperature modification device, described in more detail hereinbelow. Input apparatus 324 can be configured as, for example, a touch screen, a key pad, one or more knobs, one or more buttons, and the like to enter instructions for operation of glove 320, as described in more detail hereinbelow.

Figure 20:
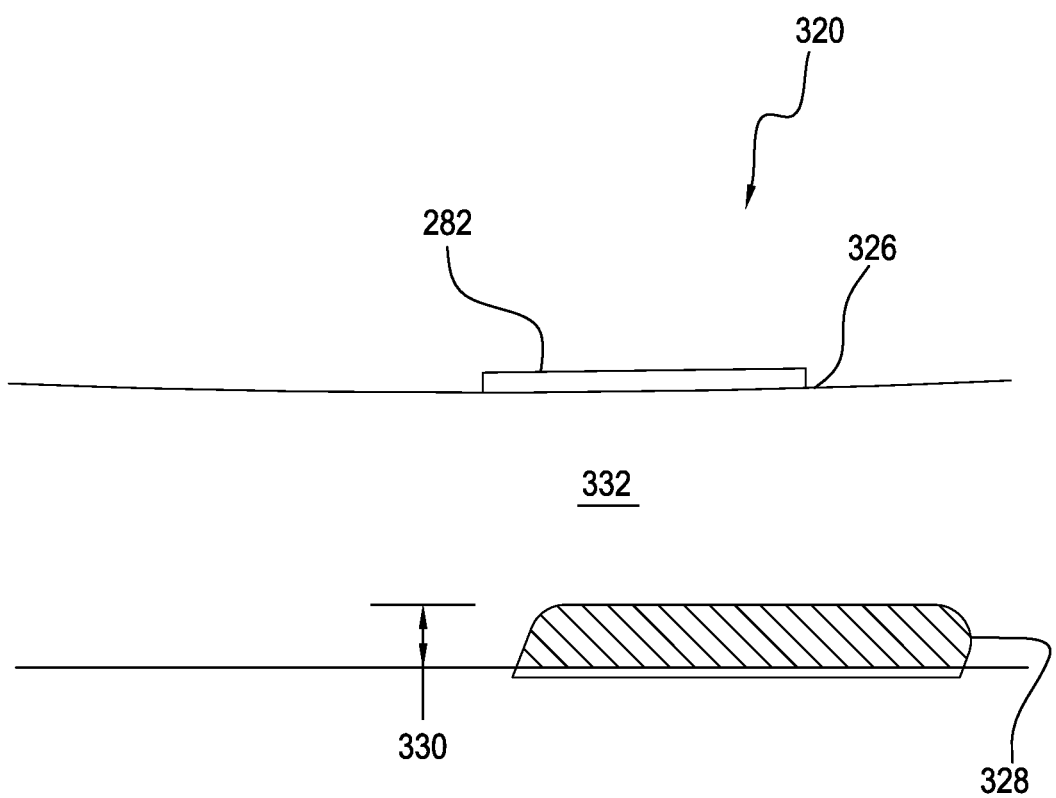
FIG. 20 shows a sectional view of the glove of FIG. 19 along the lines 20-20.
Figure 21:
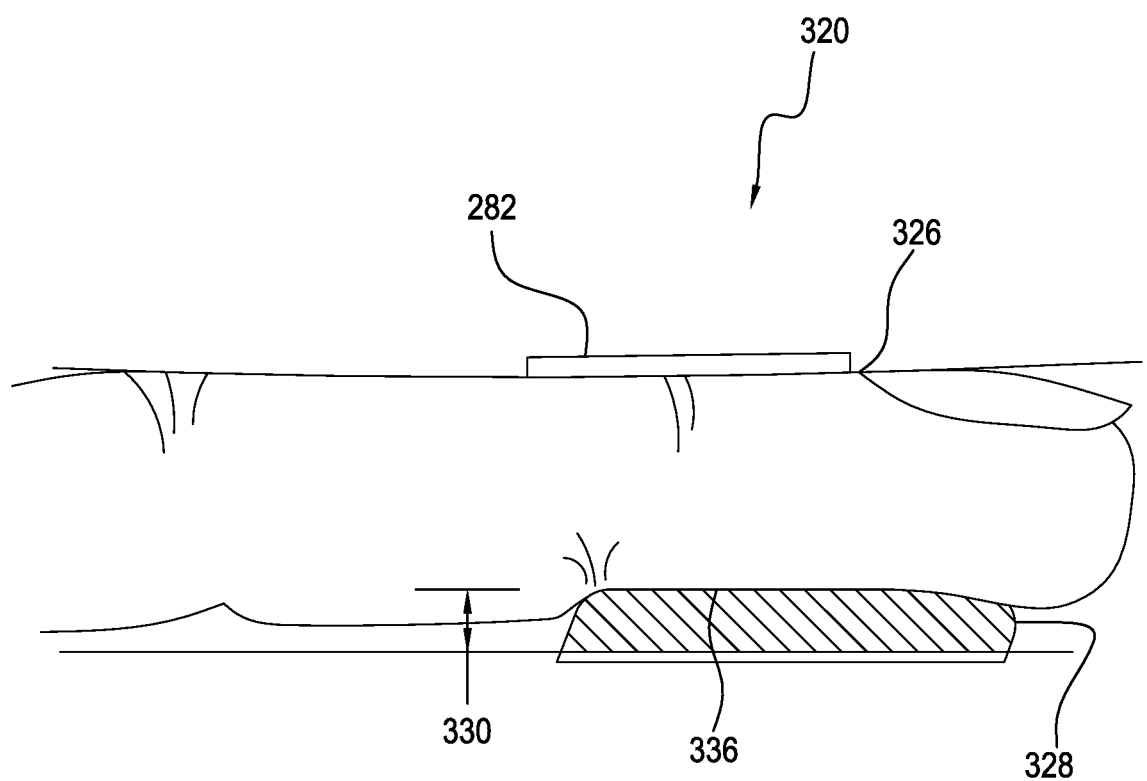
FIG. 21 shows the sectional view of FIG. 20 with a finger positioned in the glove.

FIG. 20 shows a sectional view of glove 320 of FIG. 19 along the lines 20-20. Glove 320 includes an exterior surface 326. In an exemplary embodiment, a temperature sensor, such as temperature sensor 282, can be positioned on exterior surface 326. Glove 320 further includes a temperature modification device 328 that is raised or extended to protrude a spaced distance 330 into an interior space 332 of glove 32. By protruding spaced distance 330, into interior space 332, which reduces the volume of interior space 332, temperature modification device 328 is configured to provide an affirmative contact with a finger 334, as shown in FIG. 21, causing an indentation or depression 336 in finger 334. Indentation 336 activates mechanoreception in finger 334, which in turn inhibits potential pain sensation as a result of a thermal stimulation.

Figure 22:
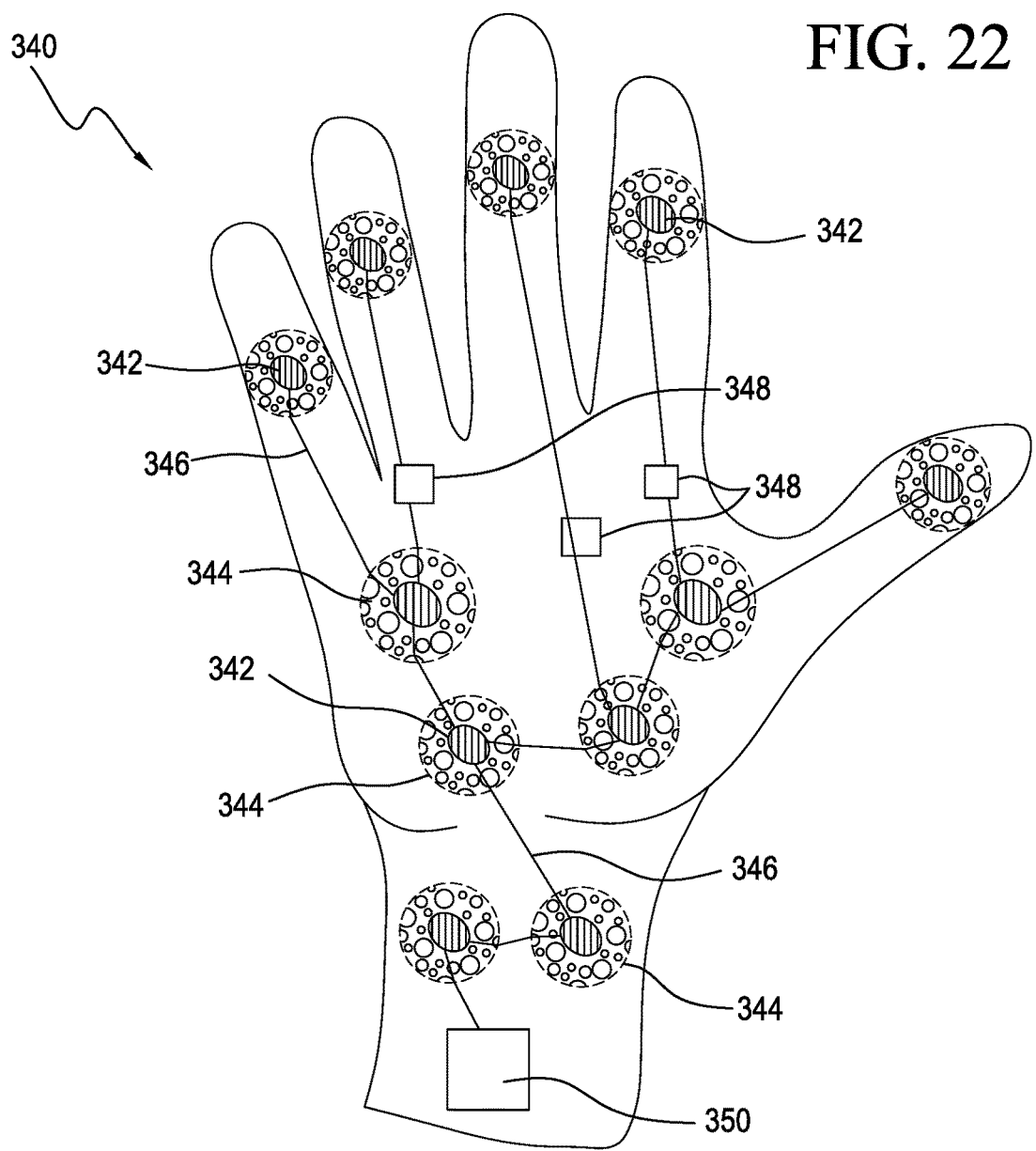
FIG. 22 shows a view of a glove in accordance with yet another exemplary embodiment of the present disclosure.
Figure 23:
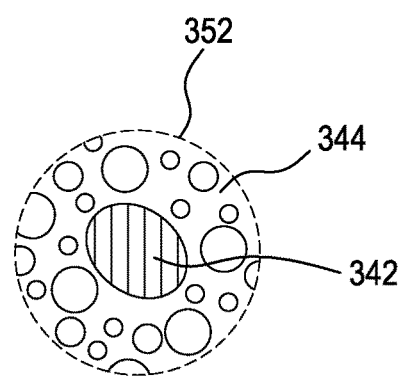
FIG. 23 shows a portion of the glove of FIG. 22.

FIG. 22 shows a view of a glove, indicated generally at 340, in accordance with yet another exemplary embodiment of the present disclosure. Glove 340 includes highly localized or separate islands of temperature modification devices 342, shown in more detail in FIG. 23. Glove 340 further includes a gel, a compressible material, or springs 344 that surround each temperature modification device 342. Gel 344 can be contained in a compliant, compressible, or flexible pouch 352. Gel 344 biases or forces each temperature modification device 342 against the skin of a hand in a manner similar to that of temperature modification device 328 shown in FIG. 20. Gel 344 activates mechanoreception by pressing temperature modification devices 342 against the skin. In this embodiment, temperature modification devices 342 have a non-raised flat surface. Pressing the gel mechanically, such as by hand, will move temperature modification devices 342 against the skin, generating motion, thereby activating mechanoreceptors and at the same time thermal stimulation of the skin of the hand. Glove 340 further includes wires 346 that connect temperature modification devices 342 to sensors 348, which can be temperature sensors, and to a processor and electronics 350.

Figure 24:
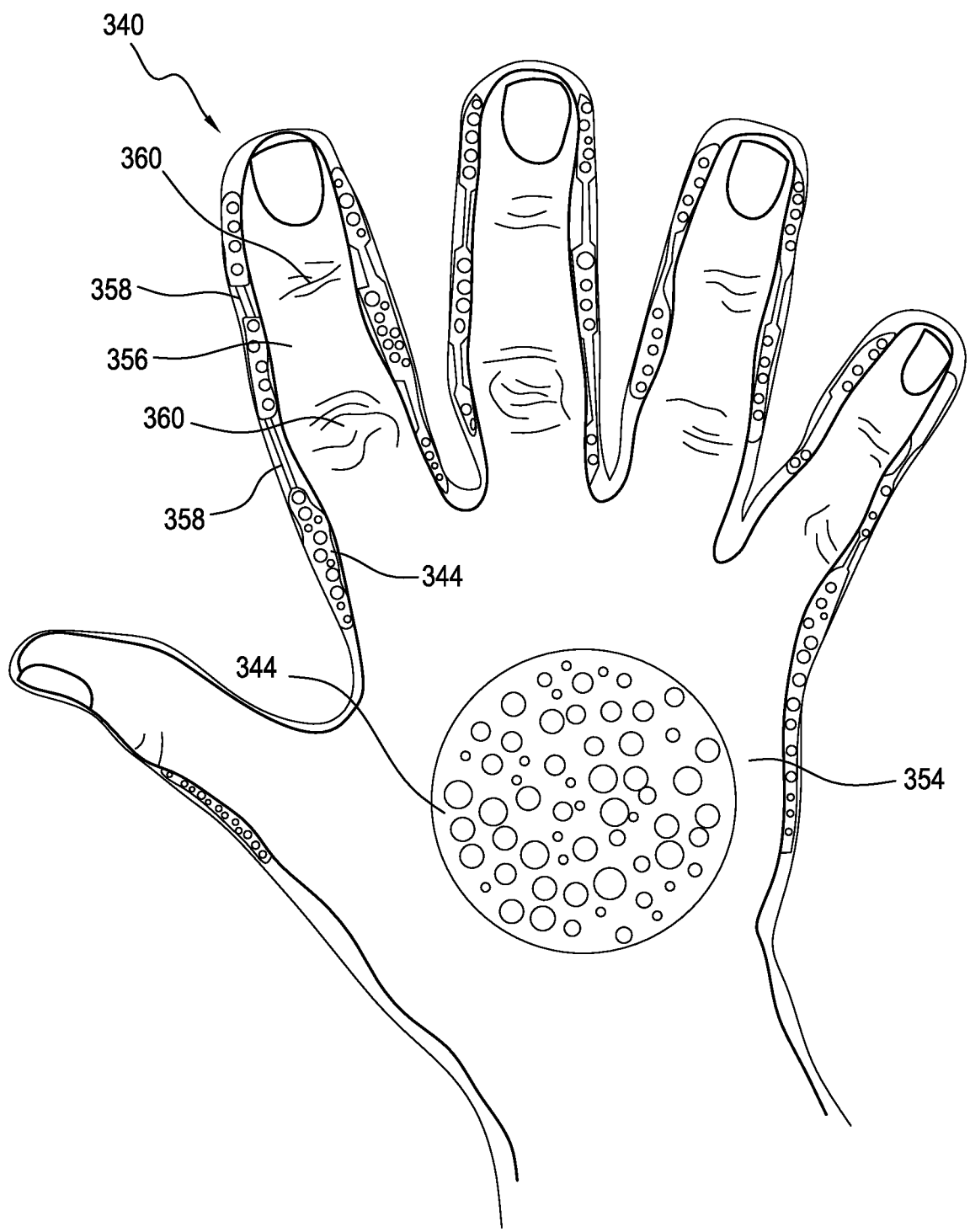
FIG. 24 shows a sectional view of the glove of FIG. 22 with a hand positioned in the glove.

FIG. 24 shows a view of glove 340 sectioned in a plane parallel to the page of the figure, with a hand 354 positioned in the glove. Gel packs 344 are shown positioned in exemplary locations in glove 354, in particular in a region along the phalanges of digits or fingers 356, with a flexible connecting portion 358 connected to each gel pack 244, particularly in the areas along bone joints 360.

Figure 25:
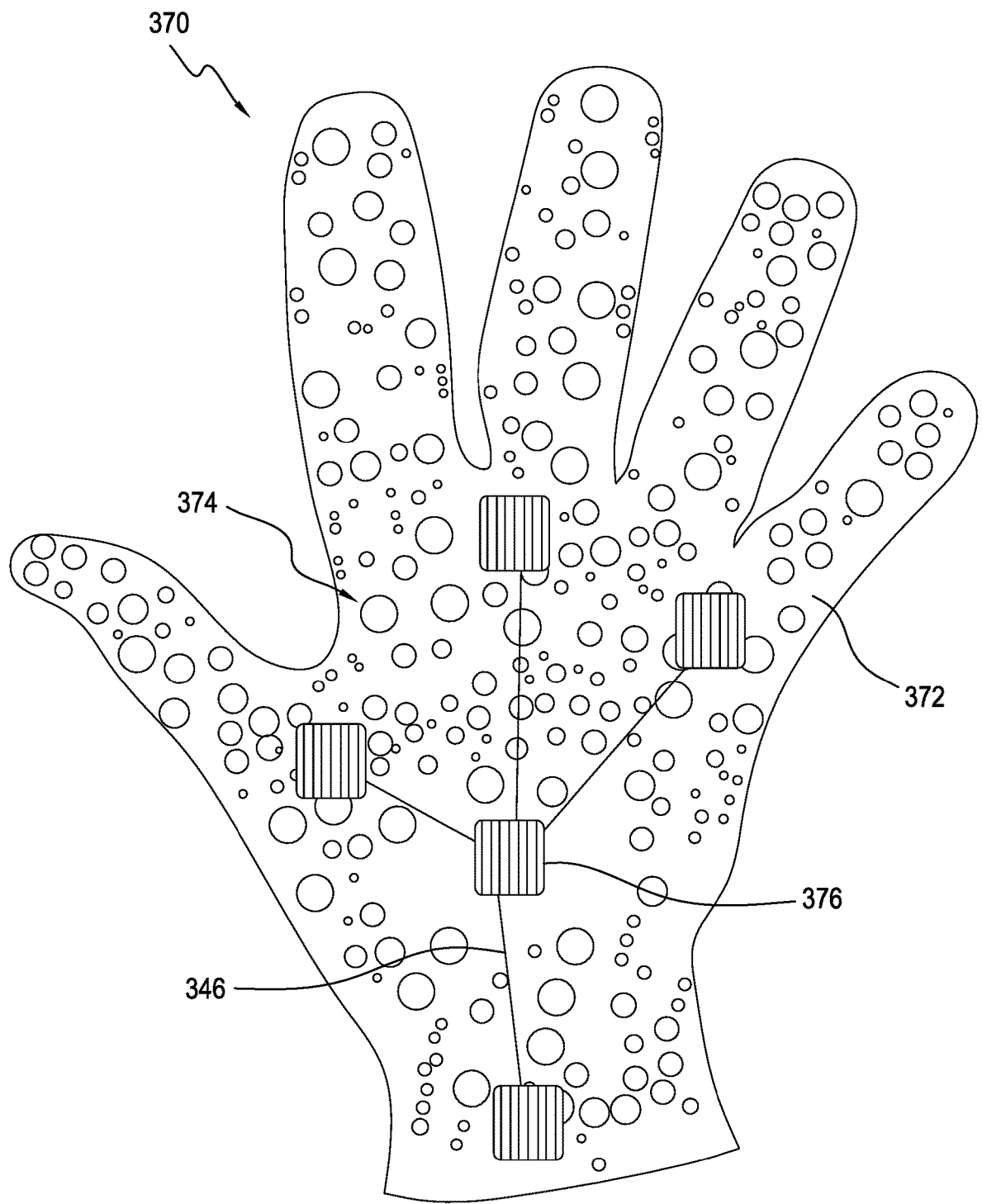
FIG. 25 shows a view of a glove in accordance with yet a further exemplary embodiment of the present disclosure.

FIG. 25 shows a view of a glove, indicated generally at 370, in accordance with yet a further exemplary embodiment of the present disclosure. Glove 370 includes a glove liner 372 containing a thermally retentive material 374 and a plurality of temperature modification devices 376 that modify the temperature of thermally retentive material 374.

Figure 26A:
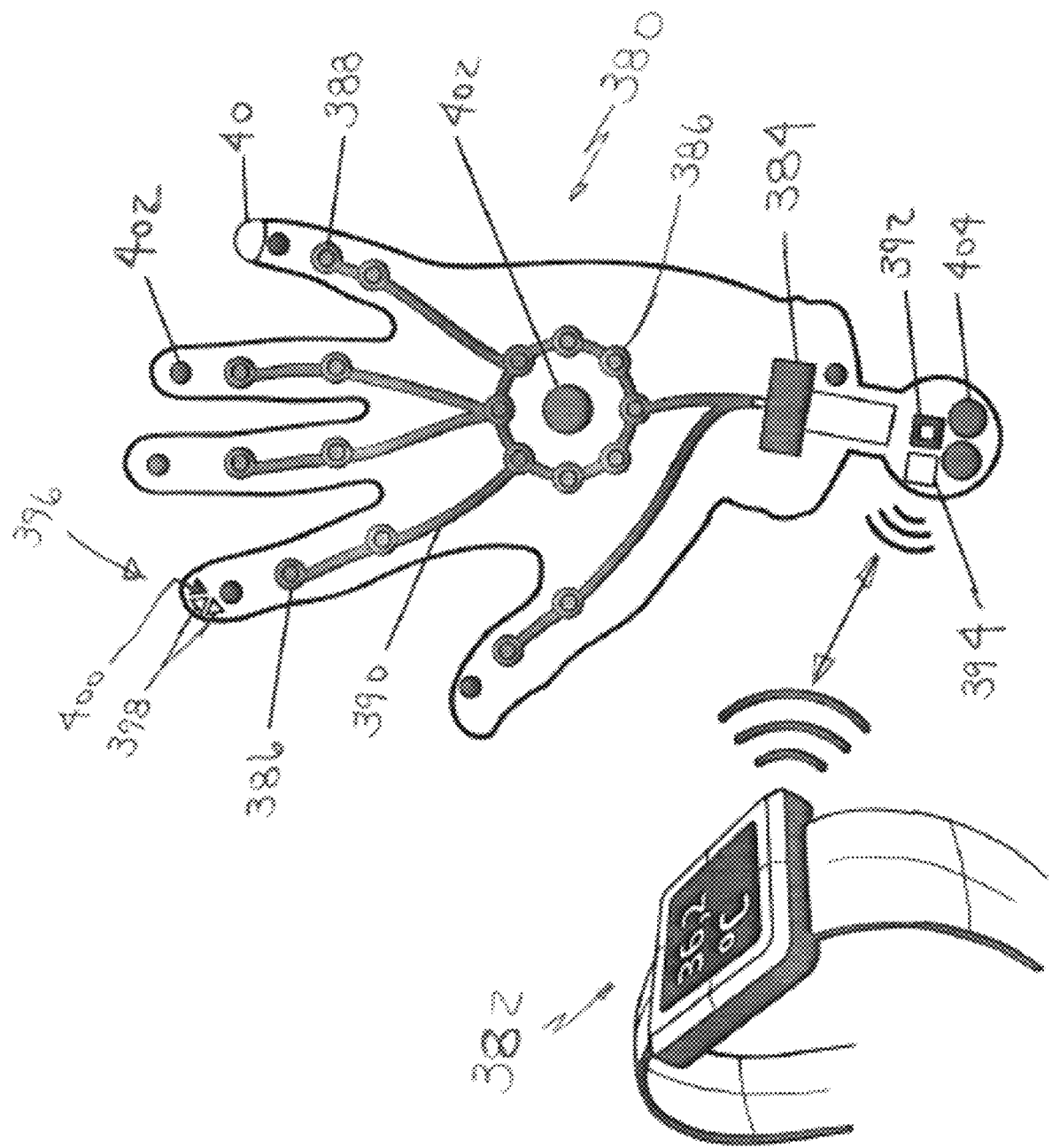
FIGS. 26A and 26B show views of a glove and a watch in accordance with a still further exemplary embodiment of the present disclosure.
Figure 26B:
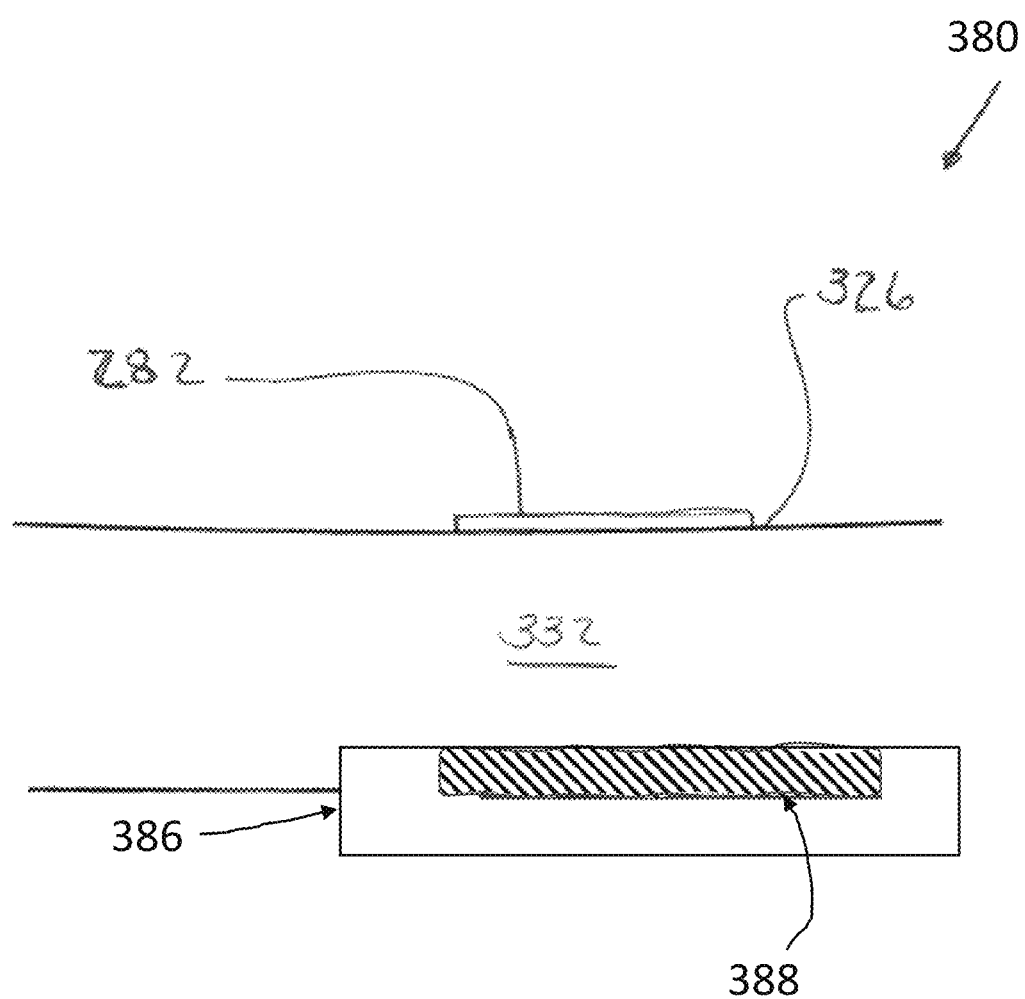

FIGS. 26A and 26B show views of a glove, indicated generally at 380, and a separate or remote electronic device, indicated generally at 382, in accordance with a still further exemplary embodiment of the present disclosure. Glove 380 includes an air pump 384, which can be a micro air diaphragm pump; a plurality of air compartments, chambers, or bags 386, each of which contains a temperature modification device 388; a plurality of air channels, passages, or paths 390 connecting air pump 384 to each of the plurality of air compartments 386; a processor 392, which can be connected to a transceiver 394, a pulsimeter and oximeter 396 that can include one or more emitters 398 and a detector 400 and that are disposed on an inner surface of glove 380, one or more temperature sensors 402; and a power supply 404 to provide electrical power to the electrically devices of glove 380. Transceiver 394 is configured to connect glove 380 to a remote electronic device 382, such as watch, cell phone, tablet, computer, and the like. Transceiver 394 can be, for example, a Blue Tooth device or other near field device. In operation, air pump 384 provides pressurized air to air channels 390 and air compartments 386, which pressurizes air compartments 386, expanding air compartments 386. The expansion of air compartments 386 cause each respective temperature modification device 388 to move toward interior space 332 and a hand positioned in interior space 332 of glove 380, reducing the volume of interior space 332 and causing each temperature medication device 388 to contact and cause a small indentation in the hand, such as that shown in FIG. 21. Such indentation provides the benefits described elsewhere herein. It should be understood that the air pump 384, air compartments 386, and air channels 390 can be replaced by a fluid pump, fluid compartments, and fluid lines or channels. The signals transmitted by transceiver 394 to and from separate electronic device 382 can be used to control the devices of glove 380, and provide a display for functions of glove 380, including temperature, pulse, and oximetry.

Figure 27:
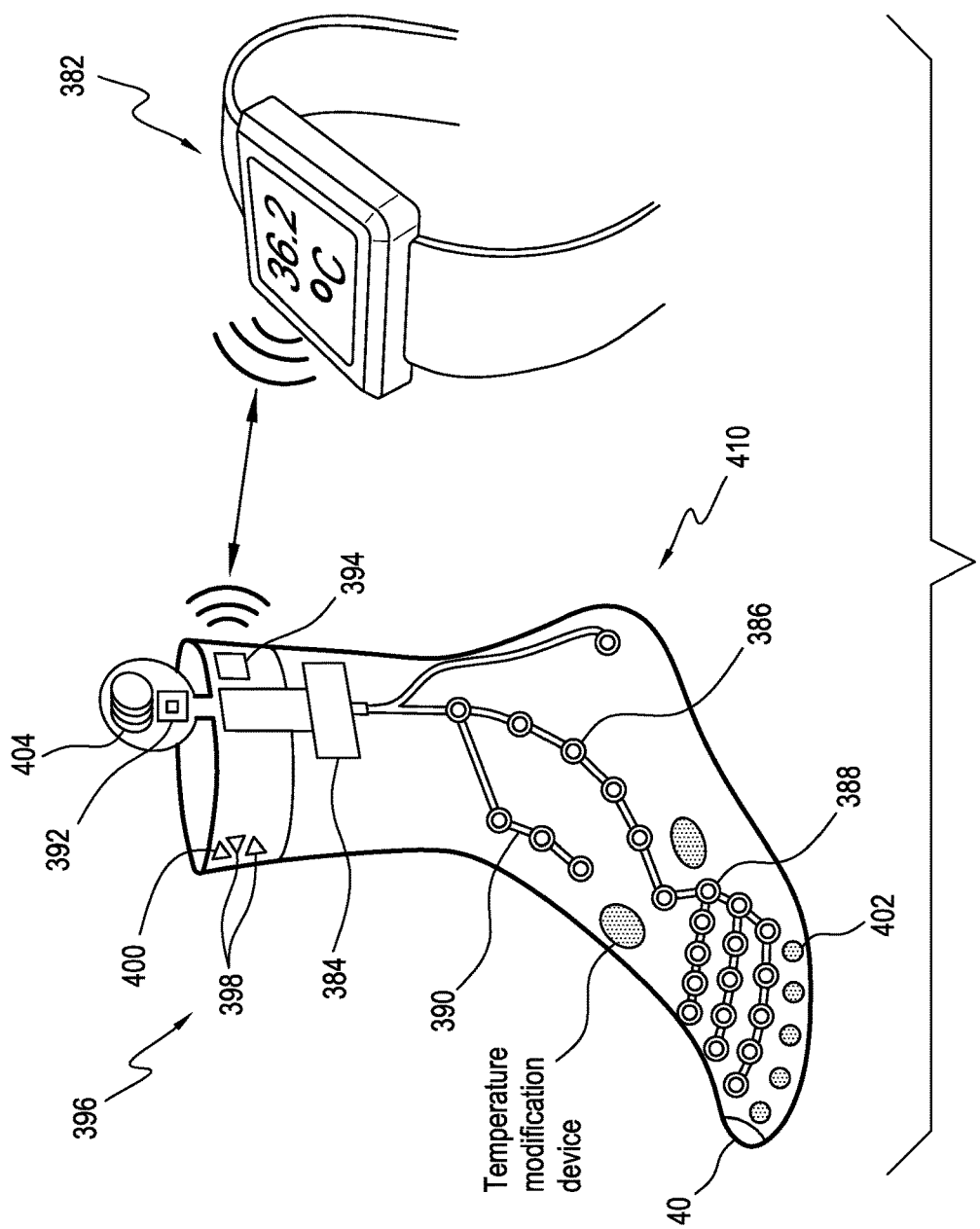
FIG. 27 shows a view of a sock in accordance with an exemplary embodiment of the present disclosure.
Figure 28:
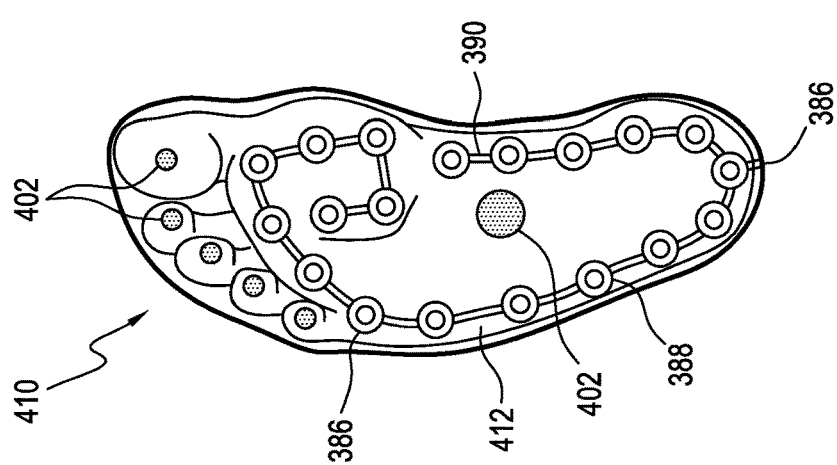
FIG. 28 shows a bottom view of the sock of FIG. 28 with the material of the sock removed to show internal features of the sock and a foot positioned in the sock.

FIGS. 27 and 28 show views of a sock, indicated generally at 410, in accordance with an exemplary embodiment of the present disclosure. Sock 410 incorporates the elements of glove 380, which are provided with the same element numbers as the elements of glove 380, and a foot 412 positioned in sock 410 accrues the same benefits as a hand positioned in glove 380.

It should be understood that temperature modification devices and sensors can be located on the dorsal and/or frontal portion of the glove and on the dorsal and/or plantar surface of the foot.

Figure 29:
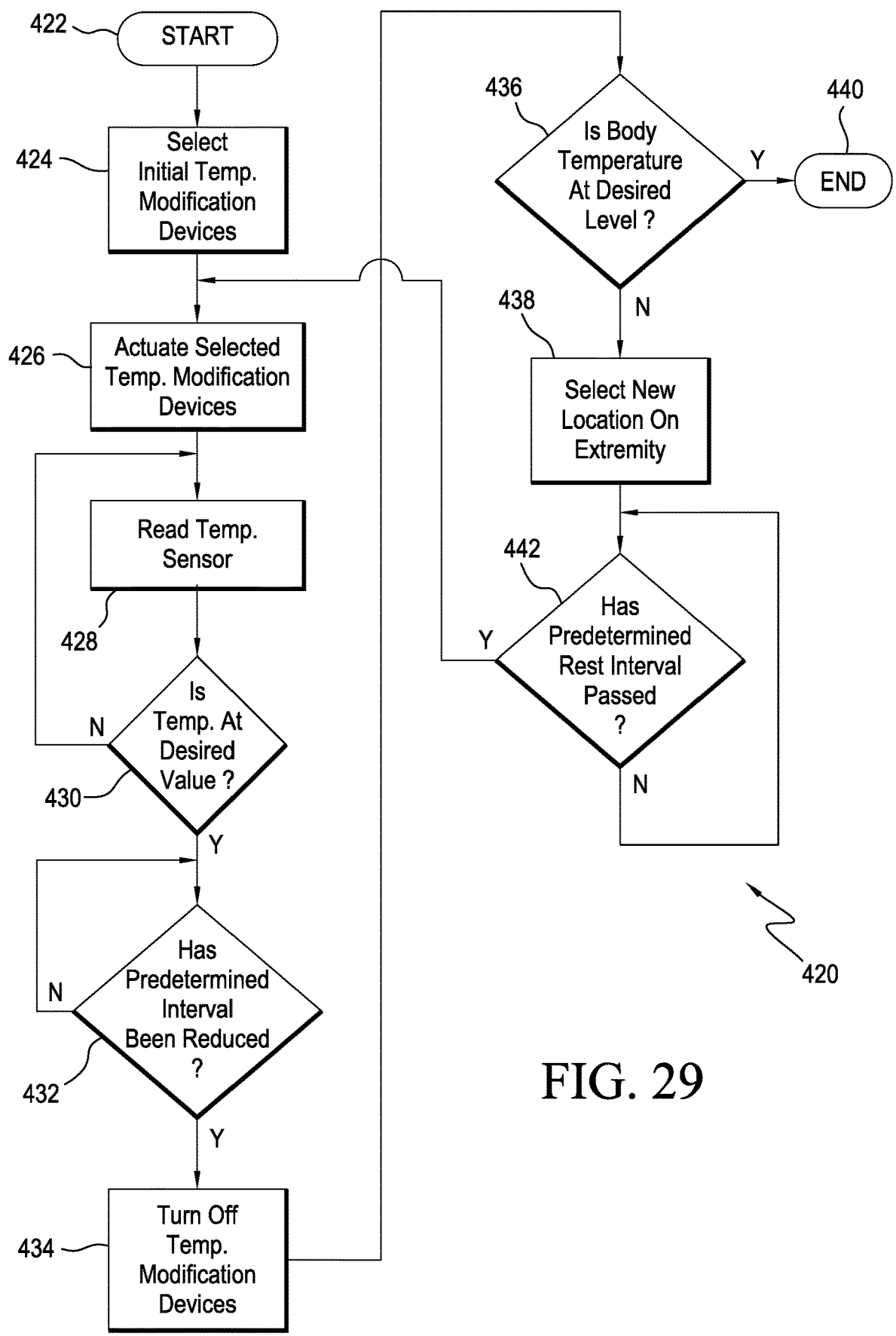
FIG. 29 shows a temperature modification process in accordance with an exemplary embodiment of the present disclosure.

FIG. 29 shows a temperature modification process, indicated generally at 420, in accordance with an exemplary embodiment of the present disclosure. Process 420 begins with a start process 422, in which registers can be cleared, devices can be powered, and other steps necessary to execute the steps of temperature modification process 420 can be initiated. Once star process 422 is complete, control passes from start process 422 to a select temperature modification device(s) process 424.

In accordance with an exemplary embodiment of the present invention, in select temperature modification device(s) process 424 processor 34 selects temperature modification device(s) to be activated. Control then passes from select temperature modification device(s) process 424 to an activate selected temperature modification devices process 426.

In activate selected temperature modification devices process 426, processor 34 activates one or more temperature modification devices, such as devices 18, 110, 160, 162, 210, and 260. Control then passes from activate selected temperature modification devices process 426 to a read temperature sensor process 428.

In read temperature sensor process 428, one or more temperature sensors are read to determine whether the selected temperature modification devices are at the desired temperature, such as a temperature between 33° C. and 34° C. Control then passes from read temperature sensor process 428 to a temperature at desired value decision process 430. If the desired temperature of the selected temperature modification devices has not been reached, control passes from temperature at desired value decision process 430 to read temperature sensor process 428, and processes 428 and 430 continue until the desired temperature is reached. Once the desired temperature has been reached, control passes from temperature at desired value decision process 430 to a predetermined interval process 432.

At predetermined interval process 432, it is determined whether the thermal stimulus has been applied for a predetermined period, which can be, for example, in a range from 5 sec to 3 minutes. Other preferred periods in the range of 1 sec to 15 min can be applied, and periods of thermal stimulus are most preferably in a range from 0.5 sec to 30 minutes, and are within the scope of the disclosure. After the first thermal stimulus, control passes from predetermined interval process 432 to a turn off temperature modification devices 434, where processor 34 initiates a quiet period, in which no thermal stimulus is applied, said quiet period preferably ranging from 1 second to 60 minutes, more preferably ranging from 10 seconds to 30 minutes, and most preferably ranging from 30 seconds to 15 minutes.

To avoid excessive stimulation, a subsequent thermal stimulus to the initial thermal stimulus can be delivered to a different finger or a different portion of the finger from the location of the original stimulus. By way of example, if the middle phalanx of the index finger and of the ring finger are stimulated, then the next thermal stimulus preferably can be applied or delivered to the distal phalanx of the middle finger and of the pinky or fifth finger, thereby avoiding repetitive thermal stimulus in one area. It should be understood that the sequential, non-repetitive, thermal stimulus applies also to the palm as well as to the feet. A saltatory thermal stimulation, in which the thermal stimulus is moved or jumps from one temperature modification device to another temperature modification device, allows the skin to rest and prevents thermal damage to the skin while accomplishing increase or decrease of skin temperature.

To be clear, thermal stimulus of the hand or foot can include stimulus at a first location, followed by a rest or off interval, and another thermal stimulus of the same location. Thermal stimulus can also include stimulus at a first location on the hand or foot, then at a second location separated from the first location. These two alternatives can be combined in a single process. For example, consider four separate locations on an extremity, first location, second location, third location, and fourth location. Thermal stimulus can be applied to the first location, then the second location, followed by the third location, and then the fourth location. Thermal stimulus can then be applied to the first location again, but only after a quiet period in which no thermal stimulus is applied has passed. Applicant further recognized that subsequent quiet periods for a location can be increased since thermal stimulus effects in a relatively short period of time can be cumulative. In addition, the period in which a thermal stimulus is applied can be decreased in subsequent applications for the same reason that thermal stimulus delivered in a relatively short period of time can be cumulative. In the context of this disclosure, the term relatively short period of time applies to periods in the range from 1 second up to at least 30 minutes. Furthermore, such periods can be adjusted to be longer when considering underlying conditions, such as pre-existing thermal damage, for example, burns, scar tissue from burns, etc., fever, infection, defective thermoregulation, etc.

After the temperature modification devices are turned to an off condition, control passes from turn off temperature modification devices 434 to a body temperature level decision process 436. When external temperature or skin surface temperature reaches a certain predetermined level, then processor 34 initiates an operation to increase or decrease extremity skin temperature (hand or foot). When skin surface temperature reaches a level less than 20° C. then heating devices are activated automatically, or manually by the user, depending on the user sensation of cold. It should be understood that any level of temperature can trigger activation of heating devices or cooling devices. In an exemplary embodiment the thermoelectric devices or temperature modification devices can applied at a variety of thermal levels, ranging from 14° C. to 30° C. for cooling, and 36° C. to 46° C. for heating. It should be understood, however, that any temperature level could be used for cooling and heating the skin surface in accordance with the principles of the disclosure.

In a preferred embodiment the thermoelectric devices or temperature modification devices are resting lightly on the surface of the skin or away from the skin surface, and with stable temperature, ranging from 33° C. to 34° C. Once a certain skin temperature level is reached, then processor 34 initiates a thermal stimulus by activating a temperature modification device. Once the temperature modification device reaches a certain level, then processor 34 activates an air pump to pump air and press the temperature modification device against the skin. When a certain temperature level is reached then processor 34 deactivates the temperature modification device, and the pump is also deactivated, causing the temperature modification device to move away from skin. Then processor 34 repeats with activation of temperature modification device followed by activation of the air pump, followed by deactivation of the temperature modification device, followed by deactivation of the air pump. Thus, the temperature modification devices contacted the skin after they had been heated or cooled to a certain temperature, called herein target temperature. Processor 34 maintains the temperature modification device at the target temperature during contact with the skin. If a predetermined temperature of the extremity and/or the body has been achieved, control passes from body temperature level decision process 436 to an end process 440, which terminates process 420. If the predetermined temperature of the extremity or the body has not yet been achieved, control passes from body temperature level decision process 436 to a select new heating location process 438.

In select new heating location process 438, a location for a next cycle of heating is selected. It should be understood that the same location can be used, or a different location can be used, as described elsewhere herein. Once the next location for heating is selected, control passes from new heating location process 438 to a predetermined rest interval process 442. In predetermined rest interval process 442, it is determined whether the rest interval for the chosen heating location has passed. For example, to reduce potential thermal damage due to repeated application of heat or cooling by a temperature modification device, thermal stimulation at each site can be repeated after a 3 minute interval in which no stimulation occurs. It should be understood that any interval can be used, based on thermal sensation by the user and risk of thermal damage, and need for skin thermal change. Thermal stimulus by the temperature modification device preferably occurs in a gradual manner. For example, a preferable heating sequence is: 36° C., 37° C., 38° C., 39° C., 40° C., 41° C., 42° C., 43° C. and 44° C., and for cooling using the following sequence: 32° C., 31° C., 30° C., 29° C., 28° C., 27° C., 26° C., 25° C., 24° C., 23° C., 22° C., 21° C., 20° C., 19° C., 18° C., 16° C., 14° C., 12° C. Once the predetermined rest interval has passed, control passes from predetermined rest interval process 442 to actuate selected temperature modification devices 426, which functions as previously described.

In an exemplary embodiment, a pressure actuating device (such as a micropump, CTS series, Hargrave Technologies or Smart Products, Inc., series AP Micro Pressure pumps) applies pressure on the temperature modification device (e.g., a thermoelectric device), causing the temperature modification device to touch the skin and/or create a minor indentation on the skin. It should be understood that the temperature modification device can just touch the skin (without indentation) to transfer thermal energy from the temperature modification device to the skin, thereby changing skin temperature while pressure by a pressure actuating device (such as inflatable device) stimulates mechanoreception thereby inhibiting pain sensation due to thermal stimuli. Once the cycle temperature change in temperature modification device is followed by pressure actuating device, the cycle will repeat again, in which the temperature modification device, such as thermoelectric device, a resistor, and the like are lifted off and pushed back against the skin in a sequential manner.

A preferred embodiment includes a processor adapted to maintain skin temperature preferably between 33° C. to 35° C. by adjusting temperature of temperature modification devices to increase or decrease the temperature of the temperature modification devices until the skin temperature reaches levels between 31° C. and 37° C., preferably between 32° C. and 36° C., and more preferably between 33° C. and 35° C., and most preferably 34° C. and 34.5° C. In severe cold environments, the user can adjust temperature levels manually, or the processor can automatically adjust temperature via input received from external (environment) temperature sensors to a higher target skin temperature, and by way of example, the processor is adapted to maintain skin temperature between 35° C. to 36° C. by adjusting temperature of temperature modification devices to increase or decrease the temperature of the temperature modification devices until the skin temperature reaches levels between 33° C. and 39° C., preferably between 34° C. and 38° C., more preferably between 35° C. and 37° C., and most preferably 35.5° C. and 36° C. In severe hot environments, the user can adjust temperature levels manually, or the processor can automatically adjust temperature via input received from external (environment) temperature sensors to a lower target skin temperature, and by way of example, the processor is adapted to maintain skin temperature between 31° C. to 33° C. by adjusting temperature of the temperature modification devices to increase or decrease the temperature of the temperature modification devices until the skin temperature reaches levels between 29° C. and 35° C., preferably between 30° C. and 34° C., more preferably between 31° C. and 33° C., and most preferably 31.5° C. and 32.5° C.

It should be understood from the description herein that elements of the disclosed embodiments, such as temperature sensors, temperature modification devices, etc., are positioned on or in a body of a wearable article. It should also be understood that all embodiments can be combined to produce one single embodiment. It should further be understood that any parts of any embodiments can be combined to produce one single embodiment. It should further yet be understood that any embodiment or part of an embodiment disclosed for a hand, such as a glove, can be used in embodiments for shoes, socks and inserts, and any piece of clothing, and any embodiment or part of an embodiment disclosed for any other body part is, such as a foot, can be used in any other embodiment of wearable article, and for sake of brevity these combinations of embodiments were not repeated in the disclosure.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A wearable article comprising:
   a wearable article body;
   at least one temperature sensor positioned on or in the wearable article body to measure a temperature of a human extremity and configured to transmit a temperature signal indicative of the temperature of the human extremity;
   a plurality of temperature modification devices positioned on or in the wearable article body adjacent to the human extremity, each temperature modification device of the plurality of temperature modification devices being configured to receive a control signal and to provide temperature modification of the human extremity based on the control signal;
   a processor configured to receive the temperature signal, to determine on a basis of the temperature signal whether the human extremity requires heating or cooling, and to control the temperature modification device based at least in part on the temperature signal;

one of a transceiver, receiver, or transmitter configured for communication with a separate electronic device;

the separate electronic device being configured to manually control operation of the plurality of temperature modification devices;

an ambient temperature sensor configured to provide an ambient temperature signal to the processor indicative of an ambient temperature of the wearable article;

control of the plurality of temperature modification devices being adjusted based on the ambient temperature signal;

an interior space;

a plurality of air chambers positioned adjacent to the interior space, some of the plurality of air chambers being connected in a plurality of series, and the plurality of series-connected air chambers being connected in parallel;

an air pump; and a plurality of passages extending into and connecting the air pump to each of the plurality of air chambers, each temperature modification device contained in each one of the plurality of air chambers, and the air pump being configured to pump air into the plurality of air chambers containing the plurality of temperature modification devices to move each temperature modification device contained in the each one of the plurality of air chambers of the plurality of temperature modification devices contained within the plurality of air chambers in an inward direction toward the interior space, reducing the volume of the interior space and causing each of the plurality of temperature modification devices contained within the each one of the plurality of air chambers to move into contact with and indented into different portions of the human extremity.

2. The wearable article of claim 1, wherein the temperature modification device is a thermoelectric device controlled by the processor to automatically provide cooling or heating of the human extremity.

3. The wearable article of claim 1, wherein the human extremity is a hand and the wearable article is a glove.

4. The wearable article of claim 3, wherein at least one of the plurality of temperature modification devices is positioned on the glove at least on a finger.

5. The wearable article of claim 3, wherein the plurality of temperature modification devices are positioned on the glove at least on a palm.

6. The wearable article of claim 3, wherein the plurality of temperature modification devices are positioned on the glove on at least a back of the hand.

7. The wearable article of claim 1, wherein the human extremity is a foot and the wearable article is a shoe.

8. The wearable article of claim 7, wherein at least one of the plurality of temperature modification devices is positioned on the shoe at least on a toe.

9. The wearable article of claim 7, wherein the plurality of temperature modification devices are positioned on the shoe on at least a sole.

10. The wearable article of claim 7, wherein the plurality of temperature modification devices are positioned on the shoe on at least a top of the foot.

11. The wearable article of claim 1, wherein the human extremity is a foot and the wearable article is a sock.

12. The wearable article of claim 11, wherein at least one of the plurality of temperature modification devices is positioned on the sock at least on a toe.

13. The wearable article of claim 11, wherein the plurality of temperature modification devices are positioned on the sock on at least a sole.

14. The wearable article of claim 11, wherein the plurality of temperature modification devices are positioned on the sock on at least a top of the foot.

15. The wearable article of claim 1, further comprising a shoe or a sock and an insert positionable within the shoe or the sock.

16. The wearable article of claim 15, wherein at least one of the plurality of temperature modification devices is positioned on the insert at least on a toe.

17. The wearable article of claim 15, wherein the plurality of temperature modification devices are positioned on the insert on at least a sole.

18. The wearable article of claim 15, wherein the plurality of temperature modification devices are positioned on the insert on at least a ball of the foot.

19. The wearable article of claim 1, further including a power supply positioned on the wearable article body.

20. The wearable article of claim 1, wherein the extremity is a foot and the ambient temperature sensor is positioned on or near a toe.

21. The wearable article of claim 19, wherein the power supply is at least one of a battery, a controller, a processor, a transceiver, a transmitter, and a receiver.

* * * * *